United States Patent
Maclean et al.

(10) Patent No.: US 6,355,670 B1
(45) Date of Patent: Mar. 12, 2002

(54) USE OF ESTROGEN ANTAGONISTS AND ESTROGEN AGONISTS IN INHIBITING PATHOLOGICAL CONDITIONS

(75) Inventors: David B. Maclean, Providence, RI (US); David D. Thompson, Gales Ferry, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/511,806

(22) Filed: Feb. 23, 2000

Related U.S. Application Data

(63) Continuation of application No. 08/803,733, filed on Feb. 21, 1997.
(60) Provisional application No. 60/013,212, filed on Feb. 28, 1996.

(51) Int. Cl.[7] .................. A61K 31/40; A61K 31/44; A61K 31/445
(52) U.S. Cl. .................. 514/428; 514/343; 514/319
(58) Field of Search .................. 514/319, 428, 514/343

(56) References Cited

U.S. PATENT DOCUMENTS

| | | | |
|---|---|---|---|
| 4,418,068 A | 11/1983 | Jones | 424/267 |
| 4,859,585 A | 8/1989 | Sonnenschein | 435/29 |
| 5,047,431 A | 9/1991 | Schickaneder et al. | 514/648 |
| 5,254,594 A | 10/1993 | Kazuaki et al. | 514/648 |
| 5,364,791 A | 11/1994 | Vegato et al. | 435/320.1 |
| 5,384,332 A | 1/1995 | Fontana | 514/648 |
| 5,389,670 A | 2/1995 | Fontana | 514/443 |
| 5,391,557 A | 2/1995 | Cullinan et al. | 514/324 |
| 5,393,763 A | 2/1995 | Black et al. | 514/333 |
| 5,418,252 A | 5/1995 | Williams | 514/443 |
| 5,434,166 A | 7/1995 | Glasebrook | 514/317 |
| 5,439,923 A | 8/1995 | Cullinan | 514/324 |
| 5,439,931 A | 8/1995 | Sales | 514/443 |
| 5,441,964 A | 8/1995 | Bryant et al. | |
| 5,441,966 A | 8/1995 | Dodge | 514/324 |
| 5,441,986 A | 8/1995 | Thompson | 514/648 |
| 5,446,053 A | 8/1995 | Koehane | 514/324 |
| 5,447,941 A | 9/1995 | Zuckerman | 514/324 |
| 5,451,589 A | 9/1995 | Dodge | 514/324 |
| 5,451,590 A | 9/1995 | Dodge | 514/324 |
| 5,455,275 A | 10/1995 | Fontana | 514/648 |
| 5,457,113 A | 10/1995 | Cullinan | 514/319 |
| 5,457,116 A | 10/1995 | Black et al. | 514/324 |
| 5,457,117 A | 10/1995 | Black et al. | 514/337 |
| 5,461,064 A | 10/1995 | Cullinan | 514/324 |
| 5,461,065 A | 10/1995 | Black et al. | 514/324 |
| 5,462,937 A | 10/1995 | Cullinan et al. | 514/212 |
| 5,462,949 A | 10/1995 | Jones et al. | 514/324 |
| 5,462,950 A | 10/1995 | Fontana | 514/324 |
| 5,464,845 A | 11/1995 | Black et al. | 514/326 |
| 5,470,883 A | 11/1995 | Stromberg | 514/648 |
| 5,550,164 A | 8/1996 | Fontana | 514/648 |
| 5,552,412 A | 9/1996 | Cameron | |
| 6,204,286 B1 * | 3/2001 | Cameron et al. | 514/428 |

FOREIGN PATENT DOCUMENTS

| | | | |
|---|---|---|---|
| EP | 0659415 | 12/1994 | ......... A61K/31/445 |
| EP | 0659429 | 12/1994 | ......... A61K/31/445 |
| EP | 0664126 | 12/1994 | ......... A61K/31/445 |
| EP | 0635264 | 1/1995 | ......... A61K/31/135 |
| EP | 0652004 | 5/1995 | ......... A61K/31/445 |
| EP | 0659412 A | 6/1995 | |
| EP | 0659413 | 6/1995 | |
| EP | 0659414 | 6/1995 | |
| EP | 0659418 | 6/1995 | ......... A61K/31/445 |
| EP | 0659419 | 6/1995 | ......... A16K/31/445 |
| EP | 0659424 | 6/1995 | ......... A61K/31/445 |
| EP | 0659425 | 6/1995 | ......... A61K/31/445 |
| EP | 0659427 | 6/1995 | ......... A61K/31/445 |
| EP | 0659428 | 6/1995 | ......... A61K/31/445 |
| EP | 0664121 | 7/1995 | ......... A61K/31/445 |
| EP | 0664123 | 7/1995 | ......... A61K/31/445 |
| EP | 0664125 | 7/1995 | ......... A61K/31/445 |
| WO | WO 8707156 | 12/1987 | |
| WO | WO 9621656 | 7/1996 | ............ C07D/28/08 |

OTHER PUBLICATIONS

Stedman's Medical Dictionary, 25th Edition (1990), pp. 628, 676, 745, 926 and 1239.

Klaus, S. et al., "In Vivo and in Vitro Antiestrogenic Action of 3–Hydroxytamoxifen, Tamoxifen and 4–Hydroxytamoxifen," *Eur. J. Cancer Clin. Oncol.*, vol. 21, No. 8, pp. 985–990, 1985.

Eppenberger, U. et al. "Pharmacologic and Biologic Properties of Droloxifene, A New Antiestrogen," *Am. J. Clin. Oncol (CCT) 14*, Suppl. 2, pp. S5–S14, 1991.

* cited by examiner

*Primary Examiner*—Jerome D. Goldberg
(74) *Attorney, Agent, or Firm*—Peter C. Richardson; Gregg C. Benson; Todd M. Crissey

(57) ABSTRACT

The present invention provides novel methods of inhibiting pathological conditions related to organ systems which respond to estrogen agonists comprising administering to a mammal in need of such treatment an effective amount of a compound of formula I

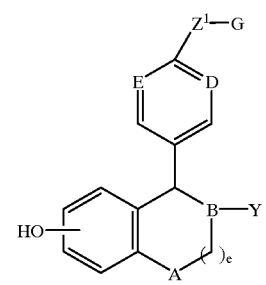

7 Claims, No Drawings

USE OF ESTROGEN ANTAGONISTS AND ESTROGEN AGONISTS IN INHIBITING PATHOLOGICAL CONDITIONS

The present application is a continuation of U.S. Ser. No. 08/803,733, filed Feb. 21, 1997, which claims the priority of U.S. provisional application No. 60/013,212, itself filed Feb. 28, 1996. The complete text and claims of the as-filed Ser. No. 08/803,733 application are hereby incorporated by reference, as if fully set forth.

This is a continuation of provisional application Ser. No. 60/013,212 filed Feb. 28, 1996, the benefit of which is hereby claimed under 37 C.F.R. §1.78(a)(3).

BACKGROUND OF THE INVENTION

Certain estrogen agonists have been reported to be useful in inhibiting pathological conditions related to organ systems which respond to estrogen agonists or antagonists. In particular, 2-phenyl-3-aroylbenzothiophenes and 1-(alkylaminoethoxy phenyl)-1-phenyl-2-phenylbut-1-enes represented by raloxifene and tamoxifen have wide application as estrogen agonists.

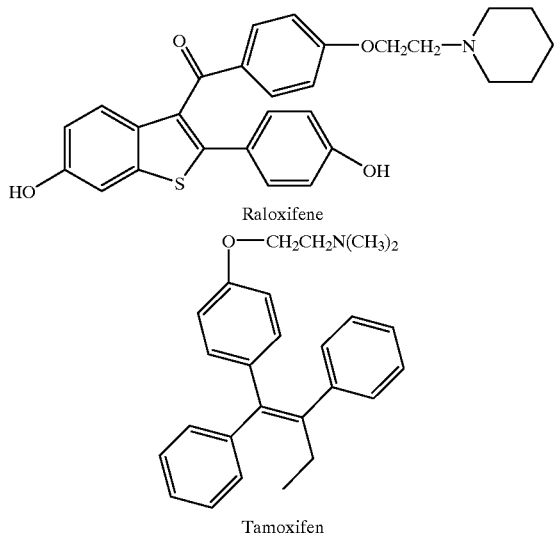

Raloxifene has been claimed to be effective in the treatment of acne, U.S. Pat. No. 5,439,923; alopecia, EP 0659414 A2; Alzheimers disease, EP 0659418 A1; atrophy of skin and vagina, U.S. Pat. No. 5,461,064; auto immune disease, EP 0664123; breast cancer, U.S. Pat. No. 4,418,068; breast disease, EP 0659419; cartilage degeneration, U.S. Pat. No. 5,418,252; CNS problems (post menopausal), 94 EP 0309470; pathology of endocrine target organs, U.S. Pat. No. 4,418,068; delayed puberty, U.S. Pat. No. 5,451,589; demyelinating disease, U.S. Pat. No. 5,434,166; dysmyelinating disease, U.S. Pat. No. 5,434,166; dysmenorrhea, U.S. Pat. No. 5,446,053; endometriosis, U.S. Pat. No. 5,461,065; female infertility, EP 659429 A1; fertility disorders; hirsutism, EP 0659414 A2; hypoglycemic, EP 635264 A2; increase libido, U.S. Pat. No. 5,439,931; inhibition of fertility, U.S. Pat. No. 5,462,949; LDL oxidation, EP 0664121 A; hypercholesterolemia, U.S. Pat. No. 5,464,845; lupus erythematosus, EP 0664125; impaired macrophage function, EP 659425 A1; male infertility, EP 0669424 A1; myocardial infaction, ischaemia, thromboembolic disorder, thrombin inhibition, EP 0664126; menopausal disorders, EP 0659415; menstruation disorders, U.S. Pat. No. 5,462,950; obesity, 94 EP 0309481; obsessive compulsive disorder, EP 0659428; osteoporosis, U.S. Pat. No. 5,457,117; ovarian dysgenesis, U.S. Pat. No. 5,451,589; peri-menopausal syndrome, U.S. Pat. No. 5,391,557; peripheral vasoconstriction, U.S. Pat. No. 5,470,883; post menopausal CNS, EP 0659415; premenstrual syndrome, U.S. Pat. No. 5,389,670; prostatic carcinoma; prostatic hyperplasia; pulmonary hypertension, U.S. Pat. No. 5,447,941; reperfusion damage, J. AM. Cardiol 25, 189A (1993); resistant neoplasm, EP 0652004 A1; restenosis, U.S. Pat. No. 5,462,937; rheumatoid arthritis, EP 0664125; seborrhea, U.S. Pat. No. 5,439,923; sexual dysfunction; sexual precocity, U.S. Pat. No. 5,451,590; thrombomodulin expression, EP 0659427; Turners syndrome, U.S. Pat. No. 5,441,966; uterine fibrosis U.S. Pat. No. 5,457,116; and vasomotor symptoms (post menopausal), 94 EP 0309473.

Tamoxifen is widely employed in the treatment of breast cancer and has been reported to be effective in the treatment of the following diseases and conditions: high lipid levels, Drug Ther. 22/3, 109 (1992); ovarian cancer, J. Clin. Oncol. 11, No. 10, 1957–68 (1993); renal cell carcinoma, Br. J. Radiol 56, No. 670, 766–7 (1983); suppression of atherogenic factor homocysteine, Env. J. Cancer 29 Suppl. 6, S110 (1993); metastatic melanoma, J. Clin. Oncol. 12, No. 8, 1553–60 (1994); mastalgia, Drugs 32, No. 6, 477–80, (1986); prolactive secreting pituitary tumors, J. Endocrinol. Invest. 3/4, 343–347 (1980); osteoporosis, Proc. Annu Meet Am Assoc. Cancer Res.; 33: A566–7 (1992); netroperitoneal fibrosis, Lancet 341, No. 8841, 382 (1993).

Small structural changes in the structure of estrogen agonists cause profound differences in biological properties. For example, droloxifene (3-hydroxytamoxifen) formula I below, has a 10–60-fold higher binding affinity to the estrogen receptor compared to tamoxifen. Droloxifene is devoid of in vivo or in vitro carcinogenic or nutagenic effects, whereas tamoxifen causes liver tumors in rats. Hasmamu, et al. Cancer Letter 84, 101–116 (1994).

Droloxifene has been reported to be effective in the treatment of breast cancer U.S. Pat. No. 5,047,431; endometriosis, U.S. Pat. No. 5,455,275; lowering cholesterol, U.S. Pat. No. 5,426,123; osteoporosis, U.S. Pat. No. 5,254,594; prostatic hyperplasia, U.S. Pat. No. 5,441,986; and restenosis, U.S. Pat. No. 5,384,332.

SUMMARY OF THE INVENTION

The present invention provides a method of Inhibiting a pathological condition which is susceptible or partially susceptible to inhibition by an antiestrogen or estrogen agonist, which comprises administering to a mammal in need of Inhibition of a pathological condition selected from the group consisting of uterine cancer, adjuvant breast cancer, breast disorder, male breast cancer, migraine, incontinence, vaginal atrophy, bladder infection, senile gynecomastia, diabetes, hypoglycemia, failure of wound healing, melanoma, impotence, inflammatory bowel disease, CNS and GI disorders caused by an excess of tackykinins, decreased libido, immune system disorders, decreased fertility, pulmonary hypertensive disease, acne, seborrhea, autoimmune disease, Turner's syndrome, alopecia, hirsutism, disorders related to an excess of neurokinin and obsessive-compulsive disorders including smoking and alcohol abuse, an effective amount of a compound of formula I

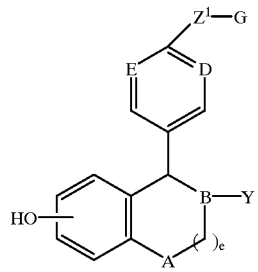

wherein:
A is selected from CH$_2$ and NR;
B, D and E are independently selected from CH and N;
Y is
(a) phenyl, optionally substituted with 1–3 substituents independently selected from R$^4$;
(b) naphthyl, optionally substituted with 1–3 substituents independently selected from R$^4$;
(c) C$_3$–C$_8$ cycloalkyl, optionally substituted with 1–2 substituents independently selected from R$^4$;
(d) C$_3$–C$_8$ cycloalkenyl, optionally substituted with 1–2 substituents independently selected from R$^4$;
(e) a five membered heterocycle containing up to two heteroatoms selected from the group consisting of —O—, —NR$^2$— and —S(O)$_n$—, optionally substituted with 1–3 substituents independently selected from R$^4$;
(f) a six membered heterocycle containing up to two heteroatoms selected from the group consisting of —O—, —NR$^2$— and —S(O)$_n$— optionally substituted with 1–3 substituents independently selected from R$^4$; or
(g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;

Z$^1$ is
(a) —(CH$_2$)$_p$W(CH$_2$)$_q$—;
(b) —O(CH$_2$)$_p$CR$^5$R$^6$—;
(c) —O(CH$_2$)$_p$W(CH$_2$)$_q$;
(d) —OCHR$^2$CHR$^3$—; or
(e) —SCHR$^2$CHR$^3$—;

G is
(a) —NR$^7$R$^8$;
(b)

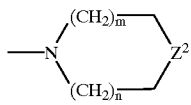

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or
(c) a bicyclic amine containing five to twelve carbon atoms, either bridged or fused and optionally substituted with 1–3 substituents independently selected from R$^4$; or Z$^1$ and G in combination may be

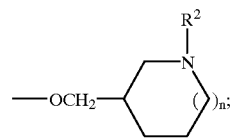

W is
(a) —CH$_2$—;
(b) —CH=CH—;
(C) —O—;
(d) —NR$^2$—;
(e) —S(O)$_n$—;
(f)

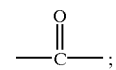

(g) —CR$^2$(OH)—;
(h) —CONR$^2$—;
(i) —NR$^2$CO—;
(j)

or
(k) —C≡C—;
R is hydrogen or C$_1$–C$_6$ alkyl;
R$^2$ and R$^3$ are independently
(a) hydrogen; or
(b) C$_1$–C$_4$ alkyl;
R$^4$ is
(a) hydrogen;
(b) halogen;
(c) C$_1$–C$_6$ alkyl;
(d) C$_1$–C$_4$ alkoxy;
(e) C$_1$–C$_4$ acyloxy;
(f) C$_1$–C$_4$ alkylthio;
(g) C$_1$–C$_4$ alkylsulfinyl;
(h) C$_1$–C$_4$ alkylsulfonyl;
(i) hydroxy (C$_1$–C$_4$)alkyl;
(j) aryl (C$_1$–C$_4$)alkyl;
(k) —CO$_2$H;
(l) —CN;
(m) —CONHOR;
(n) —SO$_2$NHR;
(o) —NH$_2$;
(p) C$_1$–C$_4$ alkylamino;
(q) C$_1$–C$_4$ dialkylamino;
(r) —NHSO$_2$R;
(s) —NO$_2$;
(t) -aryl; or
(u) —OH.
R$^5$ and R$^6$ are independently C$_1$–C$_8$ alkyl or together form a C$_3$–C$_{10}$ carbocyclic ring;
R$^7$ and R$^8$ are independently
(a) phenyl;
(b) a C$_3$–C$_{10}$ carbocyclic ring, saturated or unsaturated;
(c) a C$_3$–C$_{10}$ heterocyclic ring containing up to two heteroatoms, selected from —O—, —N— and —S—;

(d) H;
(e) $C_1$–$C_6$ alkyl; or
(f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, and quaternary ammonium salts thereof.

Preferred compounds of formula I are of the formula:

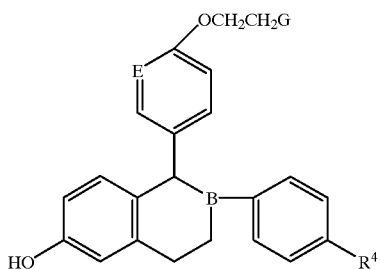

wherein G is

$R^4$ is H, OH, F, or Cl; and B and E are independently selected from CH and N.

Especially preferred compounds are:

Cis-6-(4-fluoro-phenyl)-5-[4-(2-piperidin-1-yl-ethoxy)-phenyl]-5,6,7,8-tetrahydro-naphthalen-2-ol;

(−)-Cis-6-phenyl-5-[4-(2-pyrrolidin-1-yl-ethoxy)-phenyl]-5,6,7,8-tetrahydro-naphthalen-2-ol;

Cis-6-phenyl-5-[4-(2-pyrrolidin-1-yl-ethoxy)-phenyl]-5,6,7,8-tetrahydro-naphthalen-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalen-2-ol; and 1-(4'-Pyrrolidinolethoxyphenyl)-2-phenyl-6-hydroxy-1,2,3,4-tetrahydroisoquinoline.

DETAILED DESCRIPTION OF THE INVENTION

The present invention concerns methods for inhibiting pathological conditions which are susceptible or partially susceptible to inhibition by an estrogen, antiestrogen or estrogen agonist. Such conditions include uterine cancer, adjuvant breast cancer, breast disorder, male breast cancer, migraine, incontinence, vaginal atrophy, bladder infection, senile gynecomastia, diabetes, hypoglycemia, failure of would healing, melanoma, impotence, inflammatory bowel disease, CNS and GI disorders caused by an excess of tackykinins, decreased libido, immune system disorders, decreased fertility, pulmonary hypertensive disease, acne, seborrhea, autoimmune disease, Turner's syndrome, hirsutism, disorders related to an excess of neurokinin and obsessive-compulsive disorders including smoking and alcohol abuse.

Changes in the appearance and texture of the skin with increasing age has been proverbial and well documented both quantitatively and qualitatively. It is a subject which is highly subjective in its evaluation and its ultimate effect on the individual. By in large the effect of the general atrophy of skin with age is cosmetic, but can have pathological consequences, many of which are psychological in nature, i.e., the feeling of getting "old," depression, loss of sexual attractiveness, etc. In some cases, the atrophy of the skin in older people can have direct pathologies associated with it, e.g., the ability of the skin to repair in wound healing. In general, the atrophy of the skin is considered a normal and progressive consequence of the aging process and taken with "good grace." Despite the normal acceptance of aging, there is a particular time in a woman's life, i.e., the menopause, when the progressive aging pattern is greatly accelerated, especially with regard to atrophy of the vagina and skin. It is often this rapid acceleration and suddenness of change which can be contributory to pathological and psychological distress. Additionally, vaginal atrophy can lead to discomfort, e.g., itching, dryness, and painful intercourse, which can lead to a loss of sexual enjoyment and conjugal harmony and in some cases be causal in social sequelae such as divorce.

As mentioned before, the atrophy or aging of the skin can have both qualitative and quantitative aspects. The qualitative aspects are: the change of smoothness and texture, thus causing a "roughness" in look and feel on the outer surface of the skin, the change of elasticity of the skin, thus effecting the mechanical properties of the skin, and the changes in skin pigmentation. These qualitative changes result in the commonly described condition of atrophied skin as: wrinkled, rough, withered, and spotty. Quantitatively, skin aging in post-menopausal women can be measured as: a decrease in the mitotic rate of keratinocytes, changes in dermal thickness, decrease in glycosaminoglycans and soluble collagen which are linked to the moisture content of the skin, and the decrease in the urinary excretion of hydroxyproline, a measure of decrease collagen turnover. The qualitative changes in the skin, i.e., sightlessness and mechanical properties, are the result of the quantitative changes, i.e., loss or change of the extra-cellular matrix components. Therefore, it is possible to evaluate a beneficial effect of a therapy for post-menopausal skin atrophy without totally relying on subjective analysis, even though a subjective improvement may be the ultimate desired effect. In the case of vaginal atrophy, the quantitative aspect is the amount of vaginal moisture which is controlled by the amount of secretion from glands in the dermis, the qualitative result is subjective comfort.

Currently, there are two major therapies available for the treatment of skin and vaginal atrophy in post-menopausal women. The first therapy is strictly a cosmetic approach, e.g., the use of make-up, skin moisturizers, night creams, vaginal lubricants, etc. Although this cosmetic therapy does not affect the underlying physiological cause of the atrophy, often it does achieve some subjective benefit for the individual. The second type of therapy involves the treatment of the underlying physiological causes with active, medicinal agents, most notably Vitamin A and estrogens. Vitamin A is used, its effectiveness is controversial, and it is known to have substantial, undesirable side-effects which limit its use.

At the time of menopause, the levels of estrogen produced by the ovaries rapidly decrease. This decrease in estrogen has pronounced effects on the skin and vagina causing a rapid acceleration in the natural process of atrophy. Estrogen replacement therapy is often beneficial In treating skin and vaginal atrophy. However, estrogen replacement therapy has undesired side-effects, most serious of which is the potential for the development of the threat of cancer. The inclusion of progestinal agents leads to undesirable psychological effects. The use of estrogen replacement therapy for the sole purpose of treating skin and vaginal atrophy is not common because of the negative side-effects. Clearly, an effective and safe agent which positively effects the underlying physiology and thus improves the qualitative aspects of skin and vaginal properties in post-menopausal women would be useful.

Due to the advancements in medical science, along with education, the quality and length of life have both been increased. As a result, the population, as a whole, is living longer. As such, situations which have been present but not in great numbers are becoming more numerous and recognized.

One of those situations which has been present but possibly not given enough weight is sexuality in old age. While there has always been some thought that old people are incapable of engaging in sexual activities, which is somewhat supported by a definite decline in sexuality for both sexes as they get older, sexual activity among the elderly cannot be ignored. Therefore, problems associated with such activity also cannot be ignored.

While the male, from the early and middle years, has a relatively steady decline in sexual capacity and activity, the same cannot be as convincingly said about women. There are reports that the sexual capacity of the female does not change much until late in life. (Kinsey, A. C., et al., Sexual Behavior in the Human Female, Saunders, Pa., pg. 353 (1953)). In particular, libido decreases substantially in a considerable percentage of cases after the menopause (Lauritzen et al., Estrogen Therapy the Benefits and Risks, 3rd International Workshop on Estrogen Therapy in Geneva, Oct. 20–21, 1977, Frontiers of Hormone Research, Vol. 5, pg. 10 (1978)). This belief is supported by Pfeiffer, E., et al., Terminus of Sexual Behavior in Middle and Old Age, Journal of the American Geriatric Society, pg. 2151–2158 (1972), and Pfeiffer et al., Sexual Behavior in Middle Life, American Journal of Psychiatry, 128,1262–1267 (1972). In the Pfeiffer studies, a much greater decline in both sexual activity and interest among women between the ages of 45 and 71 was found as compared to men the same age, and the most dramatic change took place between 50–60 years of age, which is, of course, generally the period during which women experience menopause or are post-menopausal. In the age group of 66–71, 50% of women said they had no or little sexual interest compared with 10% of men in the same age group.

While there has been no direct link between declining estrogen levels and declining sexuality, it has been stated that hormonal changes following a natural menopause, and certainly following surgical menopause, may contribute to the sexual decline in a portion of women. Exactly how menopause contributes to the loss of libido is not understood, yet seems fairly evident. (Bancroft, Human Sexuality and Its Problems, 2nd ed., pg. 292–293, (1989)). Therefore, it would be of use to find compounds which increase libido in post-menopausal women.

Contraceptive methods involving the administration of chemical substances are widely practiced among women who desire to limit pregnancies. Such methods control fertility through various biological mechanisms. Among the presently used chemical methods of fertility control, the most important are those which act by means of the following: (a) suppression of ovulation through inhibition of gonadotropin release; (b) alteration of the female reproductive tract to prevent migration of sperm to the site of fertilization or, if fertilization occurs, to block implantation of the zygote (nidation); (c) spermicidal action or (d) an abortifacient.

The oral contraceptives are the most prominent chemical contraceptive agents. Two types of agents are (a) estrogen combined with a progestin, and (b) a progestin alone. The contraceptives of the combined type act primarily by suppressing ovulation by negative feedback to prevent gonadotropin (LH and FSH) release by the hypothalamus, but alterations in the reproductive tract may also contribute to the antifertility effect. Such alterations include changes in the cervical mucus (which increase the difficulty of sperm migration) and in the endometrium (which decrease the likelihood of nidation). The action of a progestin alone in a very low oral dose ("mini-pill") appears to involve primarily alterations in the female reproductive tract, but ovulation suppression may also occur. Although the oral contraceptives are highly effective, their use is associated with unpleasant side effects (such as nausea, depression, weight gain, and headache) and an increased long-time risk of severe disease (such as thromboembolism, stroke, myocardial infarction, hepatic adenoma, gall bladder disease, and hypertension). Bleeding irregularities (such as breakthrough bleeding, spotting, and amenorrhea) are also frequent. A progestin, when administered alone, causes an increased incidence of changes in menstrual patterns, especially a marked increase in the amount and duration of menstrual bleeding.

Other chemical methods of contraception include the post coital administration of estrogens (e.g. diethylstilbestrol, antiprogestins, or ethynylestradiol) to prevent nidation or of prostaglandins which act as abortifacients. Both of these methods, at present, are limited to emergency situations. Still in the very early stages of development are immunological methods (vaccination) and methods involving the direct control of LHRH secretion from the pituitary by LHRH agonists or antagonists.

Another group of chemical contraceptive agents are the local spermatocides, such as nonoxynol or octoxynol, which are placed into the vagina immediately prior to coitus in the form of creams, foams, jellies, or suppositories. The spermicidal action takes place either in the vagina or elsewhere in the reproductive tract. For the latter to occur, the spermicidal agent is either absorbed on sperm membranes or is transported into the uterus under the influence of uterine contractions. The spermicidal methods are not completely reliable in preventing pregnancy and are inconvenient to use.

From the foregoing, it is evident that the presently available methods of contraception are inadequate for various reasons. Although many women practice contraception in spite of these inadequacies, a need exists in medicine for new methods.

Pulmonary hypertension represents a serious, life threatening spectrum of diseases of multiple etiology. These include congenital abnormalities of the lung, thorax and diaphragm, congenital or acquired valvular or myocardial disease, obstructive lung disease, and can be a complication of autoimmune diseases, vasculitis and collagen based diseases (Rubin, Chest. 104: 236, 1993). Patients with pulmonary hypertension frequently present with symptoms including dyspnea, fatigue, syncope, and chest pain, and have increased pulmonary artery pressure and demonstrate prominence of the main pulmonary artery, hilar vessel enlargement and decreased peripheral vessels on chest radiographs (Rich. Ann. Internal. Med., 107: 216, 1987).

While pulmonary hypertension has multiple etiologies, primary pulmonary hypertension appears to involve an autoimmune component and has been reported as a complication in patients with mixed connective tissue disease, rheumatoid arthritis, Sjogren's syndrome, systemic sclerosis and lupus (Sato, Hum. Path, 24: 199, 1993). Primary pulmonary hypertension occurs in females 1.7 times more frequently than males with the greatest predominance between the third and fourth decades of life (Rich, Ann. Internal. Med., 107: 216, 1987). The increased incidence of primary pulmonary hypertension in women of child bearing age as well as the clinical observation is that the disease can be exacerbated by pregnancy and oral contraceptives (Miller, Ann. Rheum. Dis. 46: 159, 1987; and cited in Farhat et al., J. PET., 261: 686, 1992) suggests a role for estrogen in the disease process. To this extent, Farhat et al. have demonstrated that estradiol potentiates the vasopressor response to a thromboxane mimetic in perfused rat lungs (J. PET, 261: 686, 1992). However, the role of estrogen in pulmonary hypertension is complex and may be dependent on the etiology of the disease process. In a rat model of pulmonary hypertension induced by injection of monocrotaline pyrrole (Reindel, Tax, Appl. Pharm., 106: 179, 1990) progressive pulmonary hypertension, right ventricular hypertrophy and interstitial edema around the large airways and blood vessels becomes apparent, similar to the pathology observed in man. Estradiol treatment decreased right ventricular hypertrophy and prevented interstitial edema in this model (Farhat et al., Br. J. Pharm., 110: 719, 1993) as well as attenuating the hypoxic vasoconstrictive response in isolated sheep lungs (Gordon et al., J. Appl. Physiol., 61: 2116, 1986).

Current therapy for pulmonary hypertension is inadequate and is largely dependent on the use of vasodilators, diuretics, and anticoagulants (Rubin, Drugs, 43: 37, 1992; Palevsky, JAMA, 265:1014, 1991). Vasodilators are effective in only a small subpopulation of patients with primary pulmonary hypertension and is complicated by systemic hypotensive responses. Prostacyclin infusion and high dose calcium channel blockers are also being used with limited efficacy. Heart-lung and single lung transplantation have been used on patients which do not respond to vasodilator therapy, however, due to surgical morbidity and mortality, this approach is usually limited to those patients who continue to deteriorate despite aggressive therapy at centers experienced in management of this disease. Patients frequently die of right heart failure and those individuals which have signs of right heart failure have a mean survival of 6–12 months (Rubin, Drugs, 43: 37,1992).

Therefore, pulmonary hypertensive diseases are characterized by inadequate therapies, necessity of organ transplantation and poor prognosis, and a need exits for new therapies.

Acne and seborrhea are two general classes of skin diseases which are marked by an abnormal function (usually hyperactivity) of the sebaceous glands in the skin. The subject of this invention is the use of compounds to inhibit acne and seborrhea.

Acne vulgaris is a disease of the pilosebaceous unit in the skin and is chronic and inflammatory in nature. It is characterized by comedos (blackheads), papules, pustules, cysts, and nodules. The areas of the body most commonly affected by the disease are those which have the most sebaceous glands, i.e., the face, neck, back, and chest. Acne is a very common disease in both men and women and usually appears at the beginning of puberty. Although the disease is usually mild and resolves itself by the time most people reach their midtwenties, it can in many instances be disfiguring and a source of great physiological distress. In some extreme cases, acne can be the source of severe infection and even life-threatening.

The etiology and pathogenesis of the disease begins with cohesive hyperkeratosis in which cornified cells adhere and block the follicular canal between the sebaceous gland and the surface of the skin. The sebaceous gland under hormonal control (testosterone and dihydrotestosterone) are stimulated to enlarge and produce increasing amounts of sebaceous secretions (principally in the form of triacylglycerols). These sebaceous secretions are trapped in the blocked, follicular canal and build up to form a closed comedo. At this stage, common, indigenous skin bacteria (principally, Propionibacterum Acnes) begin to metabolize the triacylglycerols to free fatty acids. These liberated fatty acids are inflammatory and results in the formation of a papule. This papule is often raised and is typical of an inflammatory lesion, i.e., red, edematous, and painful. The papule may continue to expand and rupture the follicle wall, thus forming a pustule or cyst. The pustule stage is very painful and unsightly and is often a site for secondary infection by opportunistic bacteria such as Staphofius. The pustules and cysts often lead to the scarring and disfigurement seen in severe cases of acne.

There are several drugs available for the treatment of acne. For mild cases, benzoyl peroxide is used and is often moderately effective. Benzoyl peroxide is thought to work by inhibiting cohesive hyperkeratosis and by suppressing P. Aches although benzoyl peroxide is effective in mild cases of acne, it suffers from several drawbacks: first, it must be applied topically and does not always penetrate to the pilosebaceous unit where the acne lesion initiates, second, it can cause skin irritation which can exacerbate the disease. Another moderately effective drug is vitamin A (retenoic acid, Retin A) which is used topically. Vitamin A Inhibits cohesive hyperkeratosis; however, being a topical preparation it suffers from some of the same drawbacks as benzoyl peroxide and in addition it can cause a deterioration of the protective stratum corneum if used extensively. Yet another group of commonly used drugs for the treatment of acne are antibiotics. These can be used either topically or systemically. The most commonly used antibiotics are tetracyclines and erythromycin and to a lesser extent minocycline, ampicillin, clindamycin, trimethoprim, and sulfamethoxazole. These antibiotics inhibit P. Aches and other secondary bacterial infections. There are two major drawbacks to the prolonged use of antibiotics for acne; first, the continued long exposure to antibiotics often lead to formation of resistant bacterial strains both in the skin and systemically, and second continued use of antibiotics may lead to sensitization of the patient to the antibiotic. A newer drug used for acne is Isotretinoin (Accutane, 13-cis-retenoic acid). This drug works like vitamin A; however, it can be used systemically. The side-effects of isotretinoin are often: cheilitis, a rise in serum triglycerides, elevated sedimentation rates, and most importantly, isotretinoin is a teratogen in humans and therefore cannot be used if there is a question of pregnancy during treatment. All of the above drugs have some positive effect in the treatment of acne, but each has its limiting side-effects.

Hormonal therapy is also effective for the treatment of acne in women. In many cases, the administration of estrogens has a positive effect in treating acne. Estrogens counteract the effect of endogenous androgens and therefore, decrease sebaceous excretion. However, since the use of unopposed estrogen administration in women with a uterus poses the potential for the development of endometrial cancer, a cyclic therapy of estrogen and a progestin are used for the treatment of acne. Typically, women are prescribed the normal birth control protocols for acne treatment. Although, these protocols are often effective for acne, in many cases these regiments contain progestins which have significant androgenic activity. This androgenic activity exacerbates the disease. Additionally, it is well known that progestinal agents are the cause of many negative, psychological side-effects. Clearly, a better hormonal agent would be beneficial.

Seborrhea or seborrheic dermatitis is another group of skin diseases thought to be associated with abnormal function of the sebaceous glands. It occurs in areas where there are large numbers of sebaceous glands and is characterized by flasking of the skin and red, mildly inflammatory patches. Seborrhea is most common in the hair (a form of dandruff), scalp margins, eyebrows, naso-labial folds, external ear canals, postier auricular fold, and presternal area. Generally, mild seborrhea is controlled by topical medication such as glucocorticoids and LDH in Nivea oil. However, more severe cases are more difficult to control.

There are several conditions in which the ovaries do not develop and in consequence puberty does not occur. Gonadal dysgenesis results in a severe disease state known as Turner's Syndrome resulting from the absence of a second sex chromosome (X chromosome monosomy). The syndrome is associated with the female phenotype, shortness of stature, sexual infantilism, and various somatic abnormalities. Several typical features are observed in these patients including distinct facial features, square chest, and short broad neck with webbing. Additional anomalies include cubitus valgus, congenital lymphedema of the feet and hands, renal abnormalities, high arched palate, skeletal anomalies, pigmented nevi, keloid formation, abnormal nails, and recurrent otitis media. Cardiovascular abnormalities include bicuspid aortic valves, partial anomalous venous drainage, and hypoplastic left-sided heart syndrome (Miller, M. J., et al. *J. Pedriatr.*, 102: 47–50, (1983), Mazzanti, I. et al. *Helv. Paediatr. Acta*, 43: 25–31, (1988), Van Egmond, H. et al. *Br. Heart J.*, 60: 69–71, (1988)). Renal abnormalities include rotation of the kidney, horseshoe kidney, duplication of renal pelvis and ureter, and hydronephrosis secondary to ureteropelvic obstruction.

Skeletal maturation is normal or slightly delayed in childhood but lags in adolescence as a result of gonadal steroid deficiency. Typically, fishnet appearance caused by localized rarefications occurs. Bone mineral content reduction occurs as early as 8 years of age as well as later in puberty. Changes of the spine, vertebral hypoplasia, and scoliosis are also common. Abnormalities of the carpal, wrist, knee and pelvis are also noted. The shortness of stature, including uterine growth retardation, is not evident until after the first 3 years of life after which growth velocity decelerates appreciably (Park, E., et al. *Pediatr. Res.* 17: 1–7, (1983), Lyon, A. J. et al. *Arch. Dis. Child.*, 60: 932–935, (1985)). In general, the patients suffer from sexual infantilism with genital ducts and external genitalia being immature. As a result, ovarian development is retarded.

Current therapy is directed towards correcting stature, somatic anomalies and inducing secondary sexual characteristics. Recent data indicated growth hormone is a viable therapy for stature improvement (Rosenfeld, R. G., et al. *J. Pediatr.*, 113: 393 (1988)). Patients not treated with estrogen often develop a severe form of osteoporosis similar to that experienced by females after menopause. Fractures and vertebral collapse are common. Steroid hormone therapy is normally deferred until after 15 years of age as it is believed treatment at an earlier age may result in premature maturation of the skeleton and thus a decrease in height. In fact, pharmacological doses of estrogen can accelerate bone maturation and resulting in epiphyseal fusion at an early age without concomitant increases in height. Other studies have shown low-dose estrogen allows patients to develop breasts without causing any changes in height (Alexander, R. L. et al., *Clin. Res.* 26: 174A (1978)). However, studies indicate a number of cases of endometrial cancer in patients with gonadal dysgenesis as a result of estrogen therapy (Levine, L. S., *Pediatrics*, 62: 1178–1183 (1979)).

Given the adverse side effects of estrogen in Turner's Syndrome patients, a need exists for a bone sparing agent which does not posses significant uterotrophic consequences.

In the United States, one in every four women require medical attention for breast symptomatology. While much rarer, males also encounter breast disorders. Such disorders include galactorrhea, gynecomastia, hypertrophy, polythelia, mastodynia/mastalgia, hyperprolactinermia, and generally non-fibrocystic, non-cancerous mascopathias.

Breast pain is common and estimated to be present in 50% of women. Normally the etiology is unclear. The discomfort generally is classified as (1) cyclic mastalgia or mastodynia occurring immediately prior to the menses; (2) changes in the breast such as duct ectasia and sclerosing adenosis, or (3) referred pain such as costochondritis.

Gynecomastia is enlargement of the glandular breast tissue in male humans (the female counterpart is hypertrophy). This enlargement is localized to the aureoles and can be unilateral or more commonly bilateral. The condition is usually benign in nature; however, it can be the source of severe psychological disturbance to the patient. Gynecomastia is most commonly found in males at the time of puberty, but can occur at any age. Gynecomastia can have many underlying causes, e.g., Klinefelter's syndrome (XXY chromosomal abnormality), liver disorders, estrogen therapy for prostatic carcinoma, tumors of various endocrine organs, and certain drugs (digitalis and Dilantin). The common relationship between all these causes and the resulting gynecomastia is the production of abnormal amounts of estrogens. Currently, treatment of this disease is limited to three therapies: 1) Determination and treatment of the underlying cause; 2) Surgical removal of the breast tissue; and 3) Treatment with diethylstilbestrol and radiation. Determination and treatment of the underlying cause of gynecomastia is not always possible. Surgery and treatment with diethylstilbestrol and radiation is not always successful and entails great expense and risk. Clearly, a more effective and safer therapy would be useful.

Galactorrhea is the production of breast milk in the male or female when not immediately associated with pregnancy. The highly inappropriate and rare response in the male breast is accompanied by severe psychological discomfort to the male patient. It is thought to be caused by an overproduction of estrogen and prolactin excess. Surgical treatment is usually the therapy of choice if the underlying cause can not be determined or treated. A safer and less costly therapy would be useful.

Diabetes mellitus is a systemic disease characterized by disorders in the actions of insulin and other regulatory hormones in the metabolism of carbohydrates, fats and proteins, and in the structure and function of blood vessels. The primary symptom of diabetes is hyperglycemia, often accompanied by glucosuria, the presence in urine of large amounts of glucose, and polyuria, the excretion of large volumes of urine. Additional symptoms arise in chronic or long standing diabetes. These symptoms include degeneration of the walls of blood vessels. Although many different organs are affected by these vascular changes, the nerves, eyes and kidneys appear to be the most susceptible. As such, long-standing diabetes mellitus, even when treated with insulin, is a leading cause of blindness.

There are two recognized types of diabetes. Type I diabetes is of juvenile onset, ketosis-prone, develops early in life with much more severe symptoms and has a near-certain prospect of later vascular involvement. Control of this type of diabetes is difficult and requires exogenous insulin administration. Type II diabetes mellitus is of adult onset, ketosis-resistent, develops later in life, is milder and has a more gradual onset.

One of the most significant advancements in the history of medical science came in 1922 when Banting and Best demonstrated the therapeutic effects of insulin in diabetic dogs. However, even today, a clear picture of the basic biochemical defects of the disease is not known, and diabetes remains a serious health problem. It is believed that two percent of the United States' population is afflicted with some form of diabetes. The introduction of orally effective hypoglycemic agents was an important development in the treatment of hyperglycemia. Oral hypoglycemic agents are normally used in the treatment of adult onset diabetes.

Observations in animal models on glucose metabolism for type II diabetes and in humans suggest that sex steroids play a permissive role in the phenotypic expression of hyperglycemia. These observations have prompted studies on the effects of androgens and estrogens on blood glucose levels. Testosterone administration to intact or ovariectomized female rats resulted in marked insulin resistance which correlated to morphological changes in muscle, Holmang, et al., *Am. J. Physiol.,* 259, E555–560 (1990); Holmang, et al., *Am. J. Physiol.,* 262, E851–855 (1992). In streptozotocin diabetic rats, implanted testosterone antagonized the ability of residual insulin to maintain glycemic control, Le et al., *Endocrinology,* 116, 2450–2455 (1985). In contrast, glucosuria disappeared in castrated diabetic KK mice and reappeared when androgens were replaced in these mice, Nonaka, et al., *Jpn. J. Vet. Sci.,* 50, 1121–1123 (1988): Higuichi, et al., *Exp. Anim.,* 38, 25–29 (1989).

Results from estrogen administrations also support the hypothesis that the balance between androgens and estrogens is critical to the development of hyperglycemia. Daily estradiol administrations to diabetic KK mice normalized the blood glucose levels and eliminated glucosuria, Toshiro, et al., *Jpn. J. Vet. Sci.,* 51, 823–826 (1989). Estradiol also lowered the blood glucose levels of C57BL/6J-ob/ob mice, Dubuc, *Proc. Soc. Exp. Biol. Med.,* 180, 468–473 (1985) and C57BL/KsJ db/db mice, Garris, *Anatomical Record,* 225, 310–317 (1989).

In climacteric women, anxiety, depression, tension and irritability begin during the perimenopause and can be correlated to reduce estrogen levels and estrogen replacement therapy has been recommended for the treatment of these symptoms (Malleson J., *Lancet,* 2: 158, (1953); Wilson et. al., *J. Am. Geriatric Soc.,* 11: 347 (1963)). The mechanism for protective effects of estrogen in this case in unknown, but may be related to potential effects of estrogen on biogenic amines such as serotonin (Aylward M., *Int. Res. Communications System Med. Sci.,* 1: 30 (1973)). To this regard circulating serotonin is reduced In post-menopausal women (Gonzales G., et. al., *Maturitas* 17: 23–29 (1993)), and serotonin (as well as several other biogenic amines) have a putative role in behavioral depression.

Phillips and Sherwin (Psychoneuroendocrinology, 17: 485–495 (1992)) reported that in surgically menopausal women given estrogen, scores in immediate and delayed recall tests are greater than in similar women not given estrogen. Two potential hypotheses might explain this effect. There is some evidence that partial estrogen agonists (or anti-estrogens) such as tamoxifen interact with the muscarinic receptor (Ben-Baruch G., et. al., *Molec. Pharmacol.* 21: 287–293 (1982)), and muscarinic agonists ($M_2$) are known to produce positive effects in a number of memory associated tasks and may have clinical relevance in Alzheimers Disease. Another interesting possibility may be linked to neurokinins such as Substance P, which are known to have neurotrophic as well as memory-promoting effects (Thoenen H., *Trends in Neuroscience,* 14: 165–170 (1991); Huston J. et. al., *Neurosci. Biobehav. Rev.* 13: 171–180 (1989)), thus, through an effect either at a neurotransmitter receptor in the CNS or at a neuropeptide receptor, a tissue selective estrogen agonist/antagonist could produce memory and cognitive enhancing effects. Such an activity would most relevantly be assessed in man, but a variety of animal models (i.e. maze learning, extinction etc.).are available for preclinical testing.

Perhaps the most frequent CNS related problem in climacteric women is the occurrence of hot flushes. While this undoubtedly is a somatic effect mediated by effects on the microvasculature, current evidence points strongly in the direction of CNS initiated effect (Lomax P., et. al., *Pharmac. Ther.* 57: 347–358 (1993)). Therefore, a tissue selective estrogen agonist/antagonist might offer the ideal therapy providing the desired effect in the absence of untoward side effects on reproductive tissue.

Obsessive-compulsive disorder is one of the rarer psychiatric illnesses, although minor obsessional symptoms probably occur in one-sixth of the population (*Encyclopedia of Medicine,* American Medical Association; *Current Diagnosis,* W. B. Saunders Company, 1985). It is characterized by one or both of two symptoms. The first comprises recurrent, intrusive ruminative thoughts that the patient may realize are senseless but of which he cannot stop thinking. The most common of these are thoughts of violence, contamination, doubt, or personal illness. Normally, the patient does not believe these thoughts are true reflections of reality. However, some patients become convinced that their obsessive ruminations are true, and suffer from psychotic delusions.

The second comprises repetitive, ritualistic behaviors that the patient recognizes are needless but that he cannot keep himself from performing. Hand washing, counting, checking rituals, and touching rituals are examples of such rituals. The carrying out of the ritual is not constant, but fluctuates and mirrors anxiety levels. There normally are intense feelings of panic and anxiety if the patient is prevented from completing a ritual.

While appearing depressed, a review of the history of obsessive-compulsive patients normally reveals that obsessions and compulsions precede the onset of dysphoric mood states and that depressed feelings are related to the impact the obsessive-compulsive behavior has on life. In severe cases, the patient will be incapacitated, completely overtaken by the distraction of constant obsessive ruminations or the demand to complete endless compulsive rituals.

Consumptive disorders include those disorders in which the intake, normally oral, of the amount of a substance is outside a normal range, often to an extent where health is impaired. Examples of such are eating or appetite disorders (obesity, bulimia, pica, anorexia, nervosa, and psychogenic rumination) and substance abuse or overuse (smoking, nicotine dependence, alcoholism, alcohol abuse).

It is well known that the chronic administration of nicotine results in tolerance and, eventually, dependence. The use of tobacco has become extremely widespread in all countries, despite the well known adverse effects of the use of tobacco in all its forms. Thus, it Is clear that tobacco use is extremely habit-forming, if not addictive, and that its use provides sensations to the user which are pleasant and welcome, even though the user is fully aware of the drastic long term ill effects of its use.

Cigarette smoking is the most dominant cause of preventable morbidity and early demise in developed countries. On average, smokers die several years earlier than nonsmokers and have an increased risk of fatal heart disease, lung cancer, cancers of the mouth, throat, esophagus, pancreas, kidney, bladder, and cervix, peptic ulcers and of fractures of the hip, wrist, and vertebrae. Olfaction and taste are impaired in smokers, and facial wrinkles are increased. Diabetic patients who smoke may have an increased risk of proteinuria.

Smoking cessation provides benefits, even late in life, such as reducing the risk of death or myocardial infarction in persons with coronary artery disease, reducing the progression of carotid atherosclerosis, and with reversal of chronic bronchitis.

Children of persons who smoke have lower birth weights, more frequent respiratory infections, less efficient pulmonary function, and a higher incidence of chronic ear infections than children of non-smokers and are more likely to become smokers themselves. Exposure to passive smoke has been shown, to increase the risk of cervical cancer, lung cancer, and heart disease and to promote endothelial damage and platelet aggregation.

Recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

Alcohol abuse and alcohol dependence (i.e., alcoholism) are serious public health problems of modem society. In the United States alone, an estimated 13 million adults exhibit symptoms of alcohol dependence due to excessive alcohol intake, and an additional 7 million abuse alcohol without showing symptoms of dependence according to U.S. government projections from studies conducted in the mid-1980s. Alcohol dependence and abuse are very expensive as it is estimated that it cost the U.S. well over $200 billion in 1991 with no prospect of failing or leveling off. The social and psychological damages inflicted on individuals as a consequence of alcohol abuse, e.g., children born with fetal alcohol syndrome (FAS) and victims of alcohol-related accidental death, homicide, suicide, etc., are immense.

While it is generally accepted that alcoholism and alcohol abuse are affiliations with staggering international economic, social, medical, and psychological repercussions, success in preventing or otherwise ameliorating the consequences of these problems has been an elusive goal. Only very recently the public view that alcoholism and alcohol abuse are remedial solely by moral imperatives has been changed to include an awareness of alcoholism and alcohol abuse as physiological aberrations whose etiology may be understood and for which therapy may be found through scientific pursuits. Both alcohol abuse and dependence arise as a result of different, complex, and as yet incompletely understood processes. At present, alcohol research is in the mainstream of scientific efforts.

This invention provides methods for inhibiting obsessive-compulsive and consumptive disorders.

Hirsutism (hypertrichosis) is characterized by excessive growth of hair. In women, hirsutism refers specifically to excessive growth of hair in a male pattern and distribution. Clinically, hirsutism in women is seen as a growth of terminal hair on the face (particularly on the upper lip), the chin, chest, back, and lower abdomen (escutcheon). This growth of hair is often seen as unsightly and can be the cause of embarrassment and psychological distress. Hirsutism is a common occurrence at the menopause, but can occur any time after puberty. The etiology of the condition has been linked to over production of androgens by either the ovaries or adrenal glands or both.

Hirsutism in women can be treated in a variety of ways. Cosmetic treatment of the condition, including shaving, plucking of hairs, and bleaching, while effective in improving the appearance of the patient, are only palliative and must be constantly re-applied. Glucocorticoid steroids are often effective; however, they have the potential of serious side-effects such as Cushing's Syndrome. Oral contraceptives can be effective; however, care must be taken because certain progestins used in common oral contraceptive regiments may actually contribute hirsutism because of their androgenic side-effects. Climetidine and Spironolactone have shown some effectiveness in the treatment of hirsutism; however, each of these can have unwanted side-effects. Clearly, a more effective and better tolerated agent would be useful.

Alopecia (hair loss) can occur in women for a variety of reasons, and includes female pattern alopecia. Female pattern alopecia is characterized by chronic and progressive hair loss often beginning around thirty years of age and accelerating at menopause. The hair loss is usually confined to the central scalp in a diffuse pattern. This loss of hair is cosmetically damaging and often psychologically disturbing to the patient. The etiology of the condition has been linked to an elevated level of androgens and the subsequent response of androgen sensitive hair follicles. Treatment of the condition is primarily cosmetic in nature, e.g., wigs, hair styles which cover the effected area, etc. The drug, Spironolactone, has been used, but does have side-effects. Clearly, an effective treatment for this condition would be useful.

Macrophages play a central role in host defense through a variety of effector mechanisms involving both membrane related and secretory events (Gordon et. al., *Curr. Opin. Immunol.*, 4, 25, 1992; Fuller, *Brit. Med. J.*, 48, 65, 1992). Phagocytosis, chemotaxis and antigen presentation are membrane related processes involved in immunologic defense mechanisms necessary for host survival. The importance of macrophages in defense against microbes, immune surveillance, destruction of tumor cells, and in the clearing of senescent erythrocytes has been documented in man and in animal models characterized by the selective elimination of macrophages (Claassen et. al., *J. Immunol Meth.,* 134, 153, 1990). Macrophages also contribute to host defense through secretion of bacteriostatic and bactericidal proteins, cytokines and lipid mediators, as well as oxygen and nitrogen reactive intermediates. The secretory capacity of the macrophage is central to its function as these cells secrete over 100 distinct mediators and are located in every organ (Nathan, *J. Clin. Invest.,* 79, 319, 1987).

While aberrant activation of macrophage functions is associated with autoimmune diseases as well as both chronic and acute inflammatory processes, the reciprocal condition, suppression of macrophage effector functions, is associated with reoccurring infections of both opportunistic and non-opportunistic pathogens and contributes to increased morbidity and mortality. Populations associated with an immunocompromised state include burn patients, transplants, HIV infected individuals, cancer patients undergoing chemotherapy and surgical patients, notably those with a higher risk of infection as observed in thoracoabdominal patients.

Current therapeutic approaches to these patients includes the use of intravenous infusion of macrophage derived cytokines notably the colony stimulating factors G-CSF, GM-CSF, and M-CSF (Nemunaitis, Transfusion 33: 70, 1993). Supportive therapy with antibiotics and fluids is also used, however, the limitations of these approaches are demonstrated by the continued problems of infection in immunocompromised patients and the emergence of more deadly strains of antibiotics resistant organisms. Furthermore, infections of immunocompromised patients with opportunistic pathogens including Pneumocystis and Cryptococcal infections remain significant and result in complications despite various antibiotic protocols. Clearly, novel therapeutics which can selectively enhance macrophage effector functions to augment host defense would play a central role in the clinical management of these patients.

Estrogen has been reported to increase select macrophage effector functions including Fc mediated phagocytosis, class II antigen expression, and IL-1 secretion. These observations coupled with the known propensity of women to be more resistant to a variety of infections (Ahmed et al., *Am. J. Path.,* 121, 531, 1985) suggests that estrogen-like compounds may enhance macrophage effector functions and thus be beneficial in disease states associated with depressed host defense such as bladder infections or depressed wound healing.

The term "inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

The methods of this invention are practiced by administering to an individual in need of treatment an effective amount of a compound formula I.

Compounds of formula I are described as being effective in treatment of prostate disease, breast cancer, osteoporosis, endometriosis, cardiovascular disease and hypercholesterolemia in commonly owned U.S. patent application Ser. No. 08/369,954 which is hereby incorporated by reference.

The terms $C_1$–$C_3$ chloroalkyl and $C_1$–$C_3$ fluoroalkyl include methyl, ethyl, propyl and isopropyl substituted to any desired degree with chlorine or fluorine atoms, from one atom to full substitution. The term $C_5$–$C_7$ cycloalkyl includes cyclopentyl, cyclohexyl and cycloheptyl.

Halo means chloro, bromo, iodo and fluoro. Aryl (Ar) includes phenyl and naphthyl optionally substituted with one to three substituents independently selected from $R^4$ as defined above. DTT means dithiothreitol. DMSO means dimethyl sulfoxide. EDTA means ethylene diamine tetra acetic acid.

Estrogen agonists are herein defined as chemical compounds capable of binding to the estrogen receptor sites in mammalian tissue, and mimicking the actions of estrogen in one or more tissues.

Estrogen antagonists are herein defined as chemical compounds capable of binding to the estrogen receptor sites in mammalian tissue, and blocking the actions of estrogen in one or more tissues.

One of ordinary skill will recognize that certain substituents listed in this invention will be chemically incompatible with one another or with the heteroatoms in the compounds, and will avoid these incompatibilities in selecting compounds of this invention. Likewise certain functional groups may require protecting groups during synthetic procedures which the chemist of ordinary skill will recognize.

The chemist of ordinary skill will recognize that certain compounds of this invention will contain atoms which may be in a particular optical or geometric configuration. All such isomers are included in this invention; exemplary levorotatory isomers in the cis configuration are preferred. Likewise, the chemist will recognize that various pharmaceutically acceptable esters and salts may be prepared from certain compounds of this invention. All of such esters and salts are included in this invention.

The remedies for the conditions and diseases for use in the methods of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methyicellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 0.1 mg to 50 mg in unit dosage for both oral and parenteral administration.

The active ingredient may be usually administered once to four times a day with a unit dosage of 0.1 mg to 50 mg in human patients, but the above dosage may be properly varied depending on the age, body weight and medical condition of the patient and the type of administration. A preferred dose is 0.25 mg to 25 mg in human patients. One dose per day is preferred.

Compounds used in the methods invention are readily prepared by the reactions illustrated in the schemes below.

Certain compounds of formula I are conveniently prepared from an unsaturated intermediate

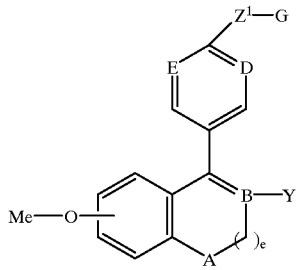

II by hydrogenation with a noble metal catalyst in a reaction inert solvent. Pressure and temperatures are not critical and hydrogenation is normally accomplished in a few hours at room temperatures at 20–80 psi hydrogen pressure.

The hydrogenated product is isolated, purified if desired, and the ether group is cleaved with an acidic catalyst in a reaction inert solvent at a temperature between 0° C. to 100° C. depending on the acidic catalyst used. Hydrogen bromide at elevated temperatures, boron tribromide and aluminum chloride at 0° C. to ambient temperature have been found to be effective for this reaction.

The product, Formula I is isolated and purified by standard procedures.

Intermediates of Formula II where A is $CH_2$, and B, D and E are CH are described in U.S. Pat. No. 3,274,213; J. Med. Chem 10, 78 (1967); J. Med. Chem 10, 138 (1967); and J. Med. Chem. 12, 881 (1969), the disclosures of which are herein incorporated by reference. They can also be prepared by procedures described below.

The preparation of the compounds of Formula I where e=1, A=$CH_2$, $Z^1$=$OCH_2CH_2$, G=cycloalkylamine, B=CH is shown in Scheme 1. Compounds 1–2, where D and E are CH are made by alkylation of 4-bromophenol with the corresponding N-chloroethylamine using potassium carbonate as base in a polar aprotic solvent like dimethylformamide at elevated temperatures. A preferred temperature is 100° C. Compounds 1–2 where D or E or both are N are synthesized using a nucleophilic displacement reaction performed on dibromides (1-1) using hydroxy ethyl cycioalkylamines under phase transfer conditions to afford bromo amines (1-2). Synthesis, 77, 573 (1980). Following halogen metal exchange using n-butyllithium or magnesium metal, bromo amines (1-2) yield the corresponding lithium or magnesium reagents which are allowed to react at low temperature in the presence of cesium chloride preferably (without cesium chloride the reaction also proceeds) with 6-methoxy-1-tetralone to afford either carbinols (1–3) or styrenes (1-4) after acidic workup. Treatment of either carbinols (1-3) or styrenes (1-4) with a brominating agent such as pyridinium bromide perbromide affords bromo styrenes (1-5). Aryl or heteroaryl zinc chlorides or aryl or heteroaryl boronic acids react with bromides (1-5) in the presence of a palladium metal catalyst like tetrakis triphenyl phosphine palladium (0) to yield diaryl styrenes (1-6). [Pure & Applied Chem. 63, 419,(1991) and Bull. Chem. Soc. Jpn. 61, 3008–3010, (1988)] To prepare the preferred compounds the substituted phenyl zinc chlorides or substituted phenylboronic acids are used in this reaction. The aryl zinc chlorides are prepared by quench of the corresponding lithium reagent with anhydrous zinc chloride. The aryl boronic acids, that are not commercially available, are prepared by quenching the corresponding aryl lithium reagent with trialkyl borate, preferably the trimethyl or triisopropyl borate, followed by aqueous acid workup. Acta, Chemica Scan. 47, 221–230 (1993). The lithium reagents that are not commercially available are prepared by halogen metal exchange of the corresponding bromide or halide with n-butyl or t-butyllithium. Alternately, the lithium reagent is prepared by heteroatom facilitated lithiations as described in Organic Reactions, Volume 27, Chapter 1. Catalytic hydrogenation of 1–6 in the presence of palladium hydroxide on charcoal, for example, affords the corresponding dihydro methoxy intermediates which were subsequently demethylated using boron tribromide at 0° C. in methylene chloride or 48% hydrogen bromide in acetic acid at 80–100° C. to afford target structures (1-7). These compounds are racemic and can be resolved into the enantiomers via high pressure liquid chromatography using a column with a chiral stationary phase like the Chiralcel OD columns. Alternately optical resolution can be carried out by recrystallization of the diastereomeric salts formed with optically pure acids like 1,1'-binapthyl-2,2'-diyl hydrogen phosphate (see Example 8).

The cis compounds (1-7) can be isomerized to the trans compounds on treatment with base (see Example 2).

When D and/or E is nitrogen the intermediates (Formula II) and compounds of Formula I may be prepared from the corresponding dihalopyridines or pyrimidines as illustrated in Scheme 1 and as fully described for 6-phenyl-5-[6-(2-pyrrolidin-1-yl-ethoxy) pyridin-3-yl]-5,6,7,8-tetrahydronaphthalen-2-ol in Example 6.

The methyl ether of the compound of Formula I where e=1, A=$CH_2$, $Z^1$=$OCH_2CH_2$, G=pyrrolidine, D,E, B=CH, Y=Ph can also be conveniently prepared by a first step of hydrogenation of nafoxidine (Upjohn & Co., 700 Portage Road, Kalamazoo, Mich. 49001) in a reaction inert solvent in the presence of a nobel metal catalyst. Pressure and temperature are not critical; the reaction is conveniently run in ethanol at room temperature for approximately 20 hours at 50 psi.

The second step is cleavage of the methoxy group which is accomplished conveniently at room temperature with an acidic catalyst such as boron tribromide in a reaction inert solvent or at 80–100° C. with hydrogen bromide in acetic acid. The product is then isolated by conventional methods and converted to an acid salt if desired.

SCHEME 1

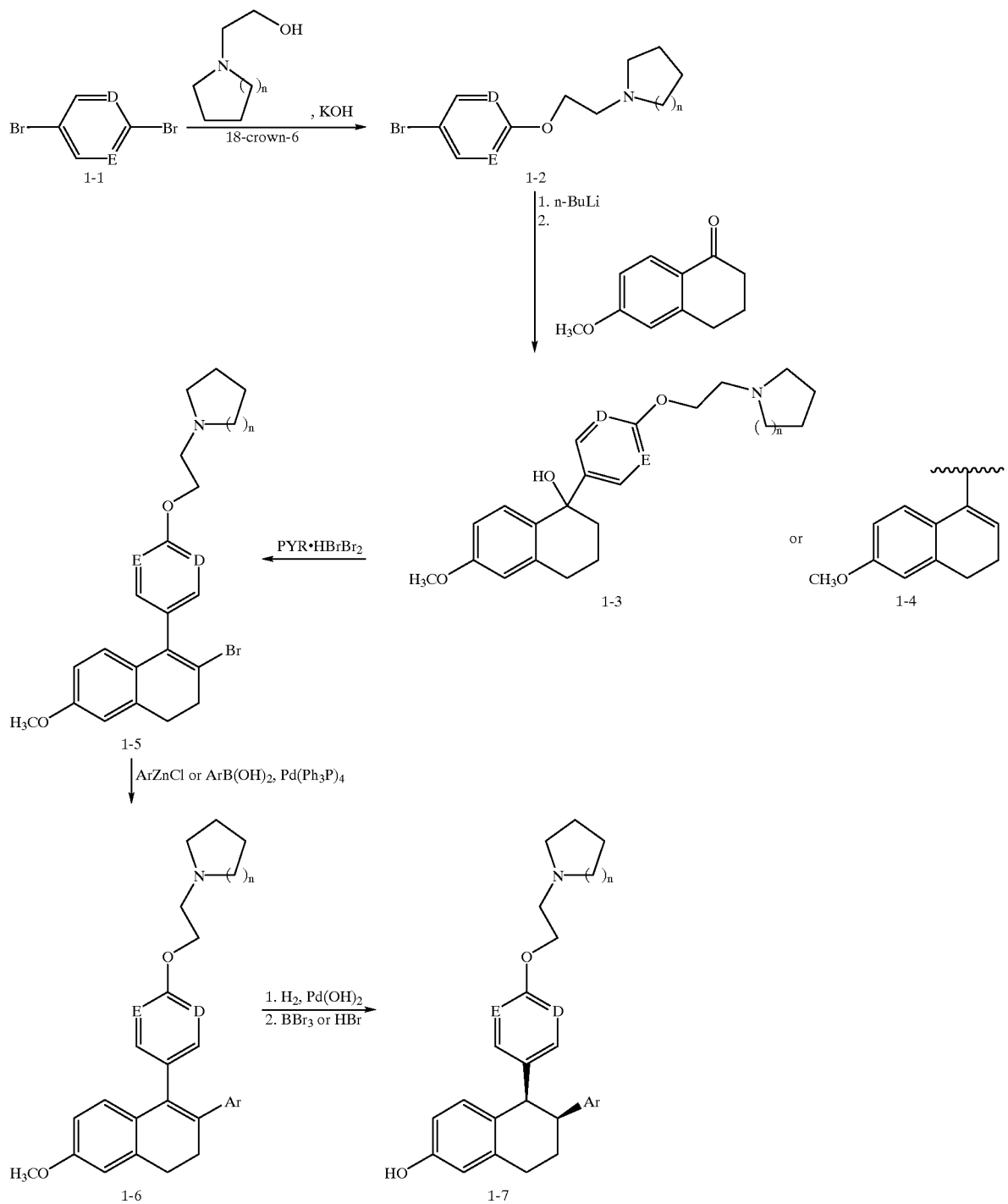

Compounds of formula I wherein B is nitrogen are prepared by the procedures illustrated in Scheme 2 and 3 and Examples 3–5 and 10–12.

The synthesis of compounds of Formula I where B=N is shown in Scheme 2. Aryl acid chlorides (2-1) on treatment with primary amines afford aryl secondary amides (2-2), which are reduced with lithium aluminum hydride in ethereal solvents to yield secondary amines (2-3). Subsequent acylation of (2-3) with aroyl acid chlorides leads to tertiary amides (2-4), which are cyclized in hot phosphorus oxychloride to yield dihydro isoquinolinium salts (2-5). Reduction with sodium borohydride to alkoxytetrahydro isoquinolines; followed by boron tribromide demethylation in methylene chloride affords the target structures.

SCHEME 2

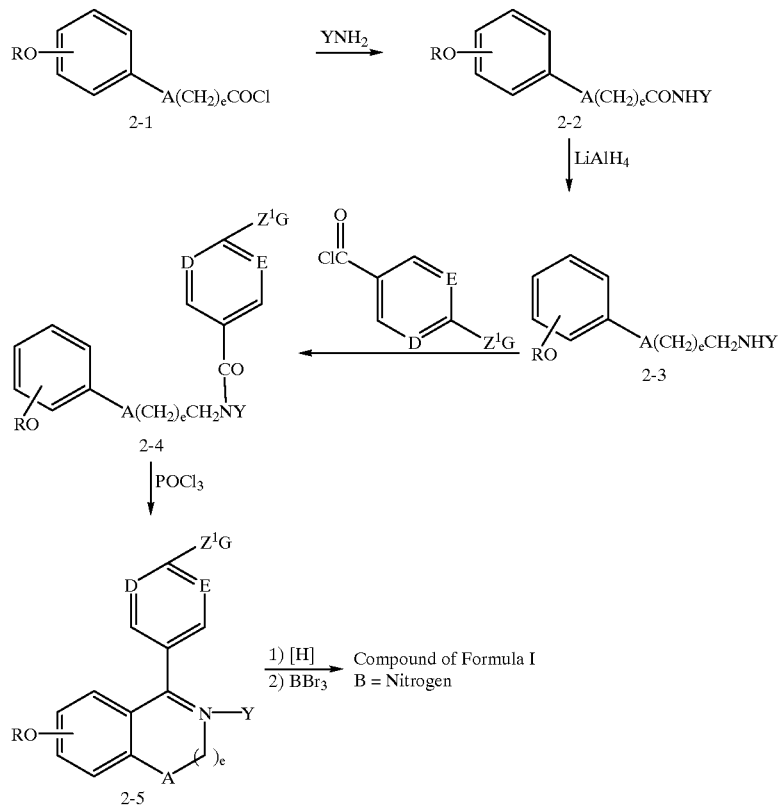

The synthesis of the compounds of Formula I where B=N is also described below in Scheme 3. Secondary amines (3-1) on acylation with benzyloxyaroyl chlorides (3-2) afford tertiary amides (3-3) which on cyclization with hot phosphorous oxychloride yield dihydro isoquinoline salts (3-4). Sodium borohydride reduction of (3-4) followed by debenzylation with aqueous hydrochloric acid affords isoquinolines (3-5), which are alkylated with the appropriately functionalized chlorides and demethylated with boron tribromide to yield the desired target structures.

SCHEME 3

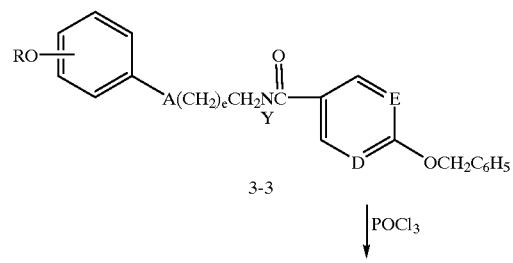

-continued

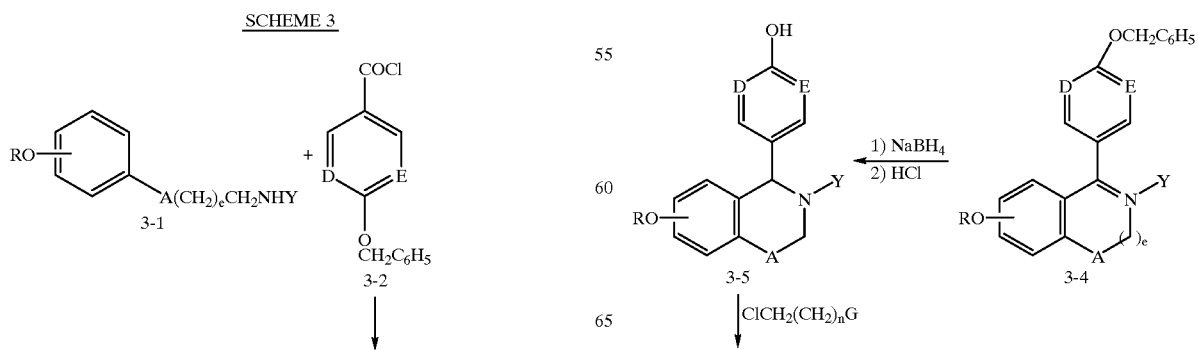

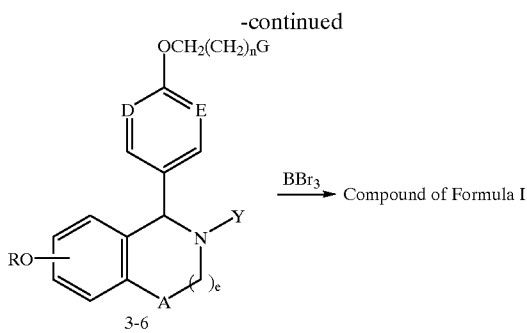

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 100 mg/day of a compound of the present invention. Preferred daily doses generally will be from about 1 mg to about 40 mg/day.

The compounds of this invention can be administered by a variety of routes including oral, rectal, transdermal, subucutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules, which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Puried Water to | 5 mL |

The medicament is passed through a No. 46 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

Antiestrogens are compounds that prevent estrogens from expressing their effects on estrogen dependent target tissues consequently antagonizing a variety of estrogen-dependent processes. However, most antiestrogens such as tamoxifen are not pure antagonists, since they exhibit some estrogenicity. The methods below enable the skilled practitioner to determine the estrogen and antiestrogen effect of the compounds of this invention. U.S. Pat. No. 4,859,585, incorporated herein by reference claims two alternative general protocols by which a substance may be characterized as an estrogen agonist and/or estrogen antagonist.

Methods to Determine Estrogenic and Antiestrogenic Potential

Uterine weight test. Compounds of Formula I are given, orally to immature female Sprague-Dawley (SD) rats (20 days old; 40 g body wt; Charles River Wiga, Sulzfeld, F.R.G.) for 3 consecutive days to test estrogenic activity. In addition to each dose of a compound of formula I, a standard dose of 1 mg/kg estradiol is administered orally to juvenile SD rats to determine the antiestrogenic effect of the compounds. The compounds are suspended in 0.25% agar for the administration. The animals are killed on day 4, the uteri removed, cleared of any intrauterine fluid and subsequently weighed in a dry condition. Estrogenic activity is estimated by the increase in uterine weight (uteroptropic effect) initiated by the respective daily doses of compounds of formula 1. The antiestrogenic effect of the compounds is tested by the reduction of the uterine weight (anti uterotropic effect) in the presence of 1 mg/kg estradiol.

Estrogen receptor-binding assay. Estrogen receptors (ER) are measured in the cytosol of uterine tissue of female immature white New Zealand rabbits (3 months of age). The uteri are separated from surrounding fatty tissue, rinsed in ice-cold phosphate-buffered saline, and immediately transferred into liquid nitrogen. The frozen uterine tissue is put into a capped Teflon cylinder pre-cooled in liquid nitrogen that is vibrated (501 {7.) for at least 30 sec. in a microdismembrator (Braun, Melsungen, F.R.G.) in the presence of a tungsten carbide bal 1. The resulting power is mixed with units (1:4/w:v) of Trisbuffer (0.01 M '1'r-is, 0.001 EDTA, pH 7.5), homogenized with a Dounce homogenizer and centrifuged at 105,000 g for 1 hr. The supernatant (cytosol) is decanted and the protein concentration adjusted to 5 mg protein/ml. The protein concentration is measured according to Lowry et al.[8]. Aliquots of cytosol are pipetted into plastic tubes, $2.5 \times 10^{-8}$M [17$\beta$-$^3$H]estradiol, and a range of concentrations of unlabeled estradiol and antiestrogens of formula I are added. The relative binding affinity of the antiestrogens to the estrogen receptor is carried out with the dextran-charcoal method at 2° C. as described by Devleeschouwer et al. [10].

All steps are carried out in triplicate. The relative binding affinity is defined as the ratio of the concentrations of radioinert 17$\beta$-estradiol to the compound of formula I that is necessary to achieve a 50% inhibition of the specific [17&3H]estradiol binding. Bound radioactivity at the highest concentration of 17/3-estradiol ($2,5 \times 1^{-7}$M) is taken as unspecific binding and subtracted from all values.

Procedures for evaluating compounds of this invention for treatment of skin and vaginal atrophy are described in U.S. Pat. No. 5,461,064, which is incorporated herein by reference.

Skin Atrophy

Three to twenty women, who are post-menopausal and in good health, are selected. Additionally, these women are selected on the basis of their presenting several signs of rapid dermal atrophy, such as a rapid increase in the number of facial wrinkles or crow's feet, rapid change in the pigmentation of the skin, i.e. "age spots", or other complaints of rapid dermal aging. It should be remembered by the attending physician that these criterion may be highly subjective to the patient and that some consideration must be taken into account in patient selection. Also, dermal atrophy may be the result of other factors such as UV damage from the sun or other environmental insults and that such patients who are suffering from these effects would be excluded.

The first component of the study is qualitative and subjective one, i.e., an evaluation of improvement in the patient's appearance. Such an evaluation requires an initial benchmark for future comparison. Some initial benchmarks might be in the form of a standardized set of questions as to how the patient views her own appearance, photographs of the patient, or a psychological profile of the patient's self-image. The second component is quantitative; these include the measurement of urinary excretion of hydroxyproline, moisture content of the skin, glycosaminoglycans in the skin, and changes in resilience and pliability of the skin. Methods for determining these factors are found in "The Menopause", Ed. R. J. Beard, University Press, Chapter 7 (1977) and "Methods in Skin Research", Ed. Skerrow, D. and Skerrow C. J., John Wiley & Sons Ltd., Chp. 22, "Analysis of Sebaceous Lipids", p. 587–608 (1985), and further references cited therein, all herein incorporated by reference. Again, an initial benchmark of these quantitative factors is obtained.

The women, thus selected and initially evaluated, are placed in a clinical protocol of receiving 20–100 mg of a compound of this invention by oral administration either as a single or split dose. Alternatively, these patients are placed in a protocol for topical administration to areas of the skin most effected by the atrophy. This topical protocol includes the use of a suitable formulation containing 5–50% (by weight) of an active compound of this invention applied to the affected area once or twice a day. Either of these protocols continues two to twelve months. Subsequent evaluations, both quantitative and qualitative, are made at appropriate intervals.

A positive result is an improvement in the overall qualitative index of the patient's appearance and/or an improvement in the quantitative parameters, e.g., an increase in the urinary excretion of hydroxyproline signifying an increase in turnover and synthesis of collagen, an increase in moisture content, glycosaminoglycans, pliability, or resilience of the skin.

Vaginal Atrophy

Three to twenty women suffering from vaginal atrophy associated with menopause are selected. These women are in general good health. Since the nature of this disorder is highly idiosyncratic and subjective, evaluation of the effectiveness of treatment would necessarily be subjective in nature. These patients are asked to keep a daily log noting such details as vaginal itching and scaling and the degree of comfort in sexual intercourse. These women are placed on a clinical protocol similar to that described above for atrophy of the skin. Particular emphasis is placed on the use of vaginal suppositories containing 5–25% of an active compound of this invention.

A positive result is an improvement in the comfort of sexual intercourse and/or a decrease in vaginal itching or scaling.

Utility of the compounds described herein is exhibited by the positive results observed in one or both of the above assays.

Procedures for evaluating the utility of a compound of this invention for increasing the libido of post-menopausal women are described in U.S. Pat. No. 5,439,931, which is incorporated herein by reference.

Assay 1

Animals used are ovariectomized or ovariectomized/ adrenalectomized Sprague-Dawley rats (Specific Pathogen Free-Anticimex, Stockholm) weighing 250–300 gms. They are housed in a room maintained at a temperature of 24° C. under reversed lighting (10 hours dark). Food and water (or saline) are available ad libitum. A compound of the invention is administered to one group of rats, and the other group is maintained as a control, and behavioral observations are made by placing each female with 2 cage-adapted, sexually experienced males for a 5-minute period during which about 20 mounts occur. The following measures are recorded:
1. Proportion of mounts by the male which elicited a lordosis response—L/M;
2. Lordosis intensity measured on a 3 point scale;
3. Lordosis duration (in seconds);
4. Female acceptance ratio—No. of mounts divided by No. of refused mounting attempts plus mounts, a measure of the female's willingness to accept the male when he attempts to mount her.

Activity of the compound is shown through positive impact on any one of the 4 observations, as compared to control.

Assay 2

Five to fifty women are selected for the clinical study. These women are post-menopausal, i.e., have ceased menstruating for between 6 and 12 months prior to the study's initiation, are in good general health, and suffer from self-described loss of libido especially noted after menopause. Because of the idiosyncratic and subjective nature of this symptom, the study has a placebo control group, i.e., the women are divided into two groups, one of which receive the active agent of this invention and the other receives a placebo. Women in the test group receive between 50–200 mg of the drug per day by the oral route. They continue this therapy for 3–12 months. Accurate records are kept as to the level of libido of the women in both groups and at the end of study these results are compared.

Activity of the compounds of the invention is illustrated by positive effects in at least one of the above assays.

Test methods for measuring the ability of a compound of this invention to inhibit fertility in women are described in U.S. Pat. No. 5,462,949, which is incorporated herein by reference.

Assay 1

Between five and fifty young adult virgin female rats weighing 200–300 g. each are separated into groups having the same number of rats. One of the groups serves as the control group and the other groups as experimental groups, each such experimental group receiving raloxifene at a particular dose level. Raloxifene is prepared in corn oil such that the daily administration is in 0.1 ml. of vehicle. The designated quantity of raloxifene in the vehicle is administered to each rat within the defined group subcutaneously (sc) daily. Alternatively, administration may be made via oral gavage or an intramuscular route. The control group receives only the vehicle. Administration of the vehicle or the combination of raloxifene and; vehicle is continued on a daily basis for 15 days. On the 5th day of treatment, one or two adult male rats weighing at least 250 g are added to each group, and cohabitation is continued until the 15th day at which time the male rats are withdrawn from the group. Each group of female rats then is maintained for an additional seven days after which the rats are sacrificed and examined for the presence of viable or resorbing fetuses.

The number of animals that exhibit evidence of pregnancy over the number of animals in the group multiplied by one hundred is the pregnancy ratio percentage (PRP). A compound is considered active when the PRP is 0 to 20%. A PRP of 40% constitutes marginal activity, and anything higher is inactive.

Assay 2

Between five and fifty young adult virgin female rats weighing 200–300 g. each are separated into groups having the same number of female rats, and paired with male rats. One of the groups serves as the control group and the other groups as experimental groups. Vaginal Smears are performed on the females daily until sperm and vaginal plugs are found, which coincides with the day of vaginal estrus and is designated day one of pregnancy.

The male rats are removed, and the experimental groups of female rats are administered raloxifene via oral garage, an intramuscular route, or by subcutaneous injection. The administration continues on a daily basis until the twelfth day of pregnancy at which time all the female rats are sacrificed and examined for the presence of implantation sites. A compound is considered active when the PRP, as defined above, is 60% or lower.

Utility of the compounds described herein is exhibited by activity in at least one of the above assays.

Procedures for determining the effectiveness of compounds of this invention in treatment of pulmonary hypertensive disease are described in U.S. Pat. No. 5,447,941, which is incorporated herein by reference.

Assay 1

The procedure as set out in Farhat et al., J PET, 261: 686 (1992) (herein incorporated by reference) is carried out. Four to thirty rats are sacrificed. The lungs are exsanguinated by perfusion via the hepatic pulmonary vein. The pulmonary artery is cannulated as is the trachea to maintain ventilation and the pulmonary cannula is connected to the perfusion line and the whole ventilated lung is removed and suspended in a perfusion chamber. The effects of vasoconstrictor substances on perfusion pressure of the isolated perfused lung is measured using a Statham pressure transducer. The increase in perfusion pressure (vasoconstriction) induced by thromboxane mimetics in the presence of estradiol is determined and the ability to block the thromboxane effects with a compound of formula I or the estradiol potentiation of the thromboxane effects will be determined.

Activity of compounds of formula I is illustrated by a reduction in pulmonary perfusion pressure increase following thromboxane mimetic stimulation.

Assay 2

Between five and fifty rats are administered a single IV dose of monocrotaline pyrrole, (3.5 mg/kg) and pulmonary disease is evaluated by histopathology, accumulation of fluorescein conjugated dextran in bronchial alveolar lavage fluid (as a measurement of pulmonary edema), and measurement of artery pressure using a Standtham P23ID pressure transducer (Reindel et al., Tax and Applic. Pharm. 106:179–200 (1990), incorporated herein by reference. A compound of formula I is administered and the effect on the rats are evaluated.

Activity of compounds of formula I is illustrated by a reduction in uptake of fluorescein conjugated dextran from bronchial alveolar lavage fluids of animals treated with a compound of formula I, indicating a reduction in pulmonary edema. Rat lungs will also be removed from thorax, perfused with modified Karnovskys fixative and processed for histopathology. A reduction in thickening of the arterial walls in treated rats is evidence for the protective role of compounds of formula I as is a decrease in pulmonary artery pressure.

Assay 3

Five to fifty women are selected for the clinical study. The women suffer from a pulmonary hypertensive disease. Because of the idiosyncratic and subjective nature of these disorders, the study has a placebo control group, i.e., the women are divided into two groups, one of which receives a compound of formula I as the active agent and the other receives a placebo. Women in the test group receive between 50–200 mg of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

The utility of a compound of this invention for inhibiting acne or seborrhea is tested by the procedures described in U.S. Pat. No. 5,439,923, incorporated herein by reference.

Assay 1

Each of from between two and twenty patients selected for the clinical evaluation is placed in a comfortable environment, i.e., comfortable temperature, humidity, lighting, etc. These patients have refrained from strenuous exercise and consumption of spicy foods for the twelve hours prior to the evaluation. An area of the body which contains a large number of sebaceous glands affected by seborrhea or acne, such as the forehead, is wiped with a gauze pad to remove accumulated lipids. A patch of the skin is taped off, forming a rectangle sized 2.5 by 1.8 cm. A pad of cigarette paper or other suitable absorbent material sixed 2.5 by 1.8 cm is placed on the test area of the skin. The absorbent material must have first been defatted with ether prior to the placement on the test area to remove background lipids. The pad is the held in place with a bandage. After fifteen minutes the pad is replaced with a fresh pad (test pad). This procedure removes the background lipids in the skin so the true rate of lipid production by the sebaceous glands may be determined. The test pad is left in place for three to six hours and then removed. The test pad is then extracted with ether to remove the lipids and the ether evaporated. The residual lipids are then weighed. The result is expressed as the number of sebaceous lipids (mg) per 10 $cm^2$ per hour. The patient then takes either 30–400 mg/day of the active ingredient by the oral route, or applies a topical formulation containing 5–20% by weight of the active ingredient daily, both for three to nine weeks. The above described test pad methodology is repeated several times throughout administration of the active ingredient to monitor progress. This assay may also be performed on animals to verify utility. A positive effect is reflected by a decrease of the rate of sebaceous gland lipid production.

Assay 2

Between two and twenty patients are enrolled in this clinical protocol and are initially evaluated by direct observation of the skin and lesions thereon. This is done by choosing one $cm^2$ sections of affected skin and the number and type of lesion (comedos, seborrheic lesions, etc.) is noted. The areas normally used are the cheeks, scalp or back. The patient then takes either 30–400 mg/day of the active ingredient by the oral route, or applies a topical formulation containing 5–20% by weight of the active ingredient daily, both for three to nine weeks. The areas of the skin being evaluated are checked during the period of administration. Care must be taken to evaluate the same areas and in order to accomplish this, a small mark or marks may be made on the skin by a permanent marker. A positive result is reflected by a reduction in the number and/or severity of the lesions in the monitored areas of the skin.

Utility of the compounds described herein is exhibited by the positive results observed in one or both of the above assays.

Utility of the compounds of this invention for treating Turner's Syndrome is determined by a procedure described in U.S. Pat. No. 5,441,966, incorporated herein by reference.

Test Procedure

Five to thirty females are selected for the clinical study. The females are between the age of twelve and eighteen and exhibit characteristics of Turner's Syndrome, but are in good general health otherwise. The study has a placebo control group, i.e., the females are divided into two groups, one of which receives the active agent of this invention and the other receives a placebo. Females in the test group receive between 10–100 mg of the active agent per day by the oral route. They continue this therapy for 3–12 months. Accurate records are kept as to the number and severity of the above mentioned symptoms in both groups and at the end of the study these results are compared. The results are compared both between members of each group and also the results for each patient are compared to the symptoms reported by each patient before the study began.

Utility of the compounds of the invention is illustrated by the positive impact they have on one or more of the symptoms when used in a study as above.

EP 0 659 419 A1 incorporated herein by reference provides methods for evaluating compounds of the present invention for breast disorders.

Assay 1

Five to fifty women are selected for the clinical study. The women have a history of a breast disorder as described herein, but are in good general health. Because of the subjective nature of these disorders, the study has a placebo control group, i.e., the women are divided into two groups, one of which receive the active agent of this invention and the other receive a placebo. Women in the test group receive between 50–200 mg of the drug per day by the oral route. They continue this therapy for 3–12 months. Accurate records are kept as to the status of the breast disorders in both groups and at the end of the study these results are compared. The results are compared both between members of each group and also the results for each patient are compared to the symptoms reported by each patient before the study began.

Utility of the compounds of the invention is illustrated by the positive impact they have on the disorder or a symptom or symptoms thereof when used in a study as above.

Assay 2

Between three and twenty male patients suffering from gynecomastia or galactorrhea are selected. Initial measurement of breast size and evidence of lactation is noted. The patients receive 30–100 mg of an active compound of this invention per day as a single or divided dose via the oral route. This treatment is continued for 3–12 months. At appropriate intervals, further measurements of breast size or evidence of lactation are being made.

Utility of the compounds of the invention is illustrated by the positive impact on the disorder or its symptoms.

A method for determining hypoglycemic activity of the compounds of this invention is set forth in EP 0 635 264 A2, incorporated herein by reference.

Five to 6 month old male, inbred viable yellow obese-diabetic mice are used. Male viable yellow mice are obese, hyperglycemic, hyperinsulinemic and insulin resistant.

Mice are housed 6 per plastic cage with bedding and fed water and Purina Formulab Chow 5008 (Purina Mills, St. Louis, Mo.) ad libitum. The temperature of the animal rooms is maintained at 23±2° C. Lights in the animal rooms were on from 0600 to 1800 h.

Antiestrogens are tested at various doses as admixtures of diets. Each dose of an antiestrogen is tested on 6 mice housed in the same cage. Compounds are mixed in pulverized chow and repelletized. Mice serving as controls are given repelletized diet without any test compound. Blood samples are collected from the tail vein immediately before and weekly after the start of a test. Blood glucose concentrations are determined by the glucose oxidase method with a model 300 Alpkem Rapid Flow Analyzer (Clackamaus, Oreg.).

Reduction of blood glucose concentration below the levels of the control is indicative of an effective antiestrogen with utility in treatment of diabetes and hyperglycemia.

The effect of compounds of the present invention on central nervous system (CNS) disorders in post-menopausal women may be evaluated by a method described in EP 0 659 413 A2, incorporated herein by reference.

Test Procedure

Five to fifty women are selected for the clinical study. The women are post-menopausal, i.e., have ceased menstruating for between 6 and 12 months prior to the study's initiation, are in good general health, and suffer from one or more of the above-mentioned CNS disorders. Because of the idiosyncratic and subjective nature of these disorders, the study has a placebo control group, i.e., the women are divided into two groups, one of which receive the active agent of this invention and the other receive a placebo. Women in the test group receive between 50–100 mg of the drug per day by the oral route. They continue this therapy for 3–12 months. Accurate records are kept as to the number and severity of the above mentioned disorders in both groups and at the end of the study these results are compared. The results are compared both between members of each group and also the results for each patient are compared to the disorders reported by each patient before the study began.

Utility of the compounds of the invention is illustrated by the positive impact they have on one or more of the CNS symptoms/disorders when used in a study as above.

Methods for evaluating the effect of compounds of this invention in treating obsessive-compulsive and consumptive disorders are described in EP 0 659 428 A1, incorporated herein by reference.

Assay 1

In order to demonstrate the in vivo effect of the compounds on alcohol consumption, experiments are designed to test the effect on free choice ethanol intake in golden hamsters. Hamsters are chosen based on previous reports that they are receptive to and give preference to high ethanol intake when compared with several other mammalian species. Kulkosky and Cornell (*Pharmacol. Biochem. & Behav.* 11: 439–44, 1979) concluded that the species differences in ethanol intake and preferences were correlated with differences in ethanol metabolism.

The animals used for the experiments described herein are two to six male adult golden hamsters. Animals are maintained on a light/dark cycle of 14 hours of light per day and for a 6-week acclimation period. Animals have access to food and water ad libitum.

For the experiment, the animals are maintained as described above in a single large cage with four 250 ml calibrated drinking bottles. The drinking bottles are fitted with stainless steel straight sipper tubes used to measure fluid consumption to the nearest 5 ml. Spillage from the drinking tubes is caught by 2 oz. jars fitted with glass funnels and positioned under the sipper tubes. Fluid consumption by the hamsters is measured once every 3 days so that the consumption volumes are large enough to obtain reasonably accurate measurements.

After a 6-week acclimation period, the body weights of the animals are taken, and water intake is noted. Water in 2 of the 4 drinking bottles is then replaced by a 15% ethanol solution and consumption of water and aqueous ethanol are measured for a period of 2 weeks. Within 2 to 3 days after the beginning of this free choice phase of feeding, the hamsters establish an explicit preference for aqueous ethanol over water and the initial preference ratio (aqueous ethanol intake divided by water intake) is noted.

As a control, the animals are then fed with 0.2 ml water twice daily, using a stainless steel animal feeding needle. Water feeding does not seem to have any effect on the animals' drinking behavior as measured by total fluid intake. After 6 days, the same group of hamsters are fed a compound of formula I via a liquid mixture for a period of 3 to 12 weeks. Activity of the compounds of formula I is illustrated by the preference ratio being lower during administration of said compound of the invention than the initial preference ratio.

Assay 2

Five to fifty women are selected for the clinical study. The women are post-menopausal, i.e., have ceased menstruating for between 6 and 12 months prior to the study's initiation, are in good general health, and suffer from either obsessive-compulsive or a consumptive disorder. Because of the idiosyncratic and subjective nature of these disorders, the study has a placebo control group, i.e., the women are divided into two groups, one of which receives raloxifene as the active agent and the other receives a placebo. Women in the test group receive between 50–200 mg of the drug per day by the oral route. They continue this therapy for 3–12 months.

Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have on one or more of the disorders/symptoms when used in an assay described above.

EP 0 659 414 A2, incorporated herein by reference describes methods for evaluating compounds of the invention for inhibition of hirsutism and alopecia.

Hirsutism

Three to twenty women suffering from hirsutism are selected. These patients are initially scored for the extent and severity of hirsutism. The clinical evaluation is made by the methods described in the reference "Methods of Skin Research," John Wiley and Sons, pp 308–318 (1985), and the references cited therein. The patients receive 10–400 mg of an active compound of this invention per day as a single or split dose by oral administration. Alternatively, they apply a 10%, by weight of active ingredient, cream or lotion once or twice a day to the affected areas. The patient continues this protocol for six months. At appropriate intervals, re-evaluation by one of the methods described above would be made.

Alopecia

Three to twenty women suffering from female pattern alopecia are selected. These patients are initially scored for the extent and severity of the alopecia. This clinical evaluation is made by the methods described in "Methods of Skin Research," John Wiley and Sons, pp 308–318 (1985) and Habif, T., "Clinical Dermatology, " C. V. Mosby Co., Chapter 23, pp 493–504 (1985); and references therein, herein incorporated by reference. Especially helpful in these evaluations is the "hair pluck" procedure and measurement of anagen to telogen ratio. The patients receive 10–400 mg of an active compound of this invention per day as a single or split dose by oral administration. Alternatively, the patients apply a 5–10% (by weight of a compound of this invention) as a cream, lotion, or shampoo to the affected area, once to twice a day. This protocol continues for six months. At appropriate intervals, re-evaluation by one of the methods described in the above references is made. A positive result is exhibited by an increase in the anagen to telogen ratio or an increase in the number of terminal hairs in the affected scalp region.

Utility of the compounds of the invention is illustrated by the positive impact they have on one or more of the symptoms when used in a study as above.

Assays which show the ability of compounds of the invention to increase macrophage function are described in EP 0 659 425 A1, incorporated herein by reference.

Assay 1

The procedure as set out in Friedman et al., *J. Clin. Invest.*, 75, 162–167 (1985) (herein incorporated by reference) is carried out, with certain modifications. Between five and one hundred mice are administered oral doses in the range of 1–10 mg/kg of a compound of formula 1 on a daily basis. Following the administration, macrophages are harvested and changes in both immune (Fc mediated) and non-immune phagocytosis are quantitated by using fluorescein conjugated yeast particles prepared based on Ragsdale, *J. Immunol. Meth.*, 123:259 (1989). For immune mediated phagocytosis, fluorescein conjugated yeast is preincubated with mouse sera to promote opsonization. Increase in fluorescence uptake by macrophages is quantitated by an increase in fluorescent emission using excitation and emission wavelengths of 482 and 520 nm, respectively. This procedure is used with ex vivo or in vitro macrophage cultures and changes in fluorescence units quantitated.

An increase in fluorescent units, as compared to control indicates activity of compounds of formula I.

Assay 2

The procedure as set out in Zuckerman et al., *Cell immunol*, 103:207, (1986); *J. Immunol.*, 140:978 (1988) (herein incorporated by reference) is carried out. The ability to induce class II antigens and consequently promote antigen presentation is determined on ex vivo primary peritoneal macrophages and in vitro with the murine macrophage cell line P388D1. Between five and one hundred mice are dosed with a compound of formula I macrophages are harvested and probed with antibodies against class II antigens of the D haplotype. Increased class II antigen expression is determined by flow cytometry using the appropriate secondary antibodies. In vitro studies evaluate the effects of the compounds in increasing the basal level and gamma interferon inducible expression of class II antigen by flow cytometry. An increase in class II expression reflect an increase in macrophage activation.

Assay 3

The procedure as set out in Seow et al., *J. Immunol. Meth.*, 98, 113 (1987) (herein incorporated by reference) is carried out. The assay is used to evaluate increases in macrophage effector functions which uses measurements of 2-deoxyglucose uptake. Macrophages ex vivo and in vivo are plated in 96 well plates at $10^5$ cells per well and incubated in phosphate buffered saline in the presence of 0.78 uCi/ml of 3H-deoxyglucose, and a compound of formula 1 is placed in the wells. Reduction in the amount of extracellular glucose reflects the uptake of this non-metabolizable glucose analog and consequently provides an independent assay for the determination of the state of macrophage activation mediated by the compound of formula 1. Increase in deoxyglucose uptake by the compound demonstrates the ability of the compounds to increase the state of macrophage activation.

Assay 4

The procedure as set out in Zuckerman, *Circ Shock*, 29, 279 (1989) (herein incorporated by reference) is carried out to illustrate the ability of the compounds of formula 1 to protect in murine sepsis and endotoxin lethality models. Between five and one hundred mice are dosed orally with 1–10 mg/kg with a compound of formula 1 for 1 week prior to sepsis challenge. Challenge is performed using a bolus IV endotoxin injection under condition in which an LD100 is achieved (200 μg lipopolysaccharide). Exogenous glucocorticoids such as dexamethasone at 20 mg/kg serve as a positive control in creasing survival. The effects of the compound of formula 1 is also determined using a sepsis model involving cecal ligation and puncture. Sepsis by both Gram positive and Gram negative organisms results in an LD100 by 48 hours despite the use of antibiotics. An increase in the number of surviving animals or in survival time, as compared to control, demonstrates the activity of the compounds.

Assay 5

The ability of the compounds of formula 1 to increase the secretion of cytokines such as TNF is quantitated in vivo by sera measurements using commercially available TNF ELISAs specific for mouse TNF. Between five and one hundred mice are orally dosed with 1–10 mg/kg of a compound of formula 1 for one week prior to injection of a lethal or sublethal dose of lipopolysaccharide (200 and 1 μg, respectively). At one hour post LPS injection the mice are bled and the basal and LPS inducible amounts of serum TNF determined. Routinely, TNF levels below 10 pg/ml are observed prior to LPS injection and achieve levels of 5–20 ng/ml following LPS. The ability of the compounds to modulate the basal or inducible levels of TNF is determined. An increase in basal TNF without triggering massive systemic TNF release in compound treated mice demonstrates the activity of the compounds in promoting cytokyne secretion. Finally, ex vivo and in vitro measurements of TNF release from peritoneal macrophages exposed to 1–5 μM of a compound in vitro is also performed by ELISA to determine the extent of cytokine increase mediated by a compound of formula 1.

Assay 6

Five to fifty women are selected for the clinical study. The women are immunosuppressed. Because of the idiosyncratic and subjective nature of these disorders, the study has a placebo control group, i.e., the women are divided into two groups, one of which receives a compound of formula 1 as the active agent and the other receives a placebo. Women in the test group receive between 50–200 mg of the drug per day. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula 1 in increasing macrophage function is illustrated by the positive impact they have in at least one of the assays described above. Such compounds are useful in combating infections and promote wound healing.

What is claimed is:

1. A method of inhibiting skin atrophy, the method comprising administering to a patient in need of said inhibition an effective amount of (−)-cis-6-phenyl-5-[4-(2-pyrrolidinyl-1-yl-ethoxy)-phenyl]-5,6,7,8-tetrahydronaphthalen-2-ol, or a an optical or geometric isomer thereof, or a nontoxic pharmacologically acceptable acid addition salt, N-oxide, ester or quaternary ammonium salt thereof.

2. The method of claim 1 wherein the patient is a post-menopausal woman.

3. The method of claim 1 wherein the inhibition of skin atrophy ameliorates wrinkles.

4. The method of claim 1 wherein the inhibition of skin atrophy ameliorates spotty skin.

5. A method of inhibiting skin atrophy which comprises administering to a mammal in need of inhibition of skin atrophy an effective amount of a compound of formula I

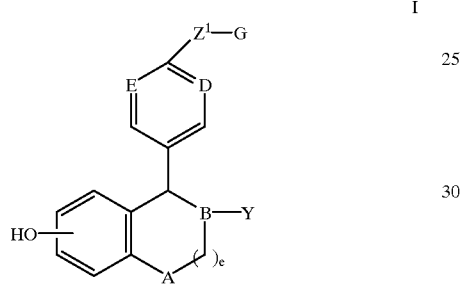

wherein:
A is CH2; B, D, and E is CH
Y is
  (a) phenyl, optionally substituted with 1–3 substituents independently selected from $R^4$;
  (b) naphthyl, optionally substituted with 1–3 substituents independently selected from $R^4$;
  (c) $C_3$–$C_8$ cycloalkyl, optionally substituted with 1–2 substituents independently selected from $R^4$;
  (d) $C_3$–$C_8$ cycloalkenyl, optionally substituted with 1–2 substituents independently selected from $R^4$;
  (e) a five membered heterocycle containing up to two heteroatoms selected from the group consisting of —O—, —$NR^2$— and —$S(O)_n$—, optionally substituted with 1–3 substituents independently selected from $R^4$;
  (f) a six membered heterocycle containing up to two heteroatoms selected from the group consisting of —O—, —$NR^2$— and —$S(O)_n$— optionally substituted with 1–3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$—, and —$S(O)_n$—, optionally substituted with 1–3 substituents independently selected from $R^4$;

$Z^1$ is
  (a) —$(CH_2)_p W(CH_2)_q$—;
  (b) —$O(CH_2)_p CR^5R^6$—;
  (c) —$O(CH_2)_p W(CH_2)_q$;
  (d) —$OCHR^2CHR^3$—; or
  (e) —$SCHR^2CHR^3$—;

G is
  (a) —$NR^7R^8$;
  (b)

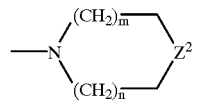

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1–3 substituents independently selected from $R^4$;

$Z^1$ and G in combination may be

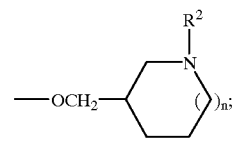

W is
  (a) —$CH_2$—;
  (b) —CH=CH—;
  (c) —O—;
  (d) —$NR^2$—;
  (e) —$S(O)_n$—;
  (f)

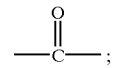

(g) —$CR^2(OH)$—;
  (h) —$CONR^2$—;
  (i) —$NR^2CO$—;
  (j)

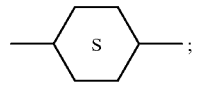

or
  (k) —C≡C—;

R is hydrogen or $C_1$–$C_6$ alkyl;
$R^2$ and $R^3$ are independently
  (a) hydrogen; or
  (b) $C_1$–$C_4$ alkyl;
$R^4$ is
  (a) hydrogen;
  (b) halogen;
  (c) $C_1$–$C_6$ alkyl;
  (d) $C_1$–$C_4$ alkoxy;
  (e) $C_1$–$C_4$ acyloxy;

(f) $C_1$–$C_4$ alkylthio;
(g) $C_1$–$C_4$ alkylsulfinyl;
(h) $C_1$–$C_4$ alkylsulfonyl;
(i) hydroxy ($C_1$–$C_4$)alkyl;
(j) aryl ($C_1$–$C_4$)alkyl;
(k) —$CO_2H$;
(l) —CN;
(m) —CONHOR;
(n) —$SO_2NHR$;
(o) —$NH_2$;
(p) $C_1$–$C_4$ alkylamino;
(q) $C_1$–$C_4$ dialkylamino;
(r) —$NHSO_2R$;
(s) —$NO_2$;
(t) -aryl; or
(u) —OH.

$R^5$ and $R^6$ are independently $C_1$–$C_8$ alkyl or together form a $C_3$–$C_{10}$ carbocyclic ring;

$R^7$ and $R^8$ are independently
  (a) phenyl;
  (b) a $C_3$–$C_{10}$ carbocyclic ring, saturated or unsaturated;
  (c) a $C_3$–$C_{10}$ heterocyclic ring containing up to two heteroatoms, selected from —O—, —N— and —S—;
  (d) H;
  (e) $C_1$–$C_6$ alkyl; or
  (f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, esters, and quaternary ammonium salts thereof.

6. A method of claim 5 wherein the compound of formula 1 is a compound of the structure

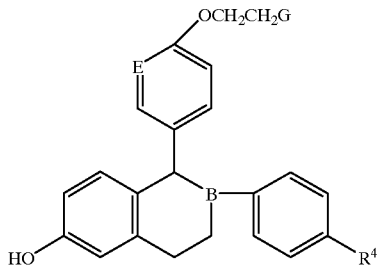

wherein G is

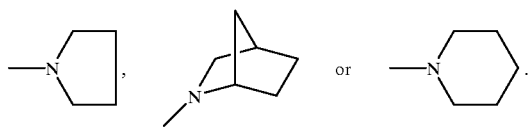

7. A method of claim 5 wherein the compound of formula 1 is selected from the group consisting of
Cis-6-(4-fluoro-phenyl)-5-[4-(2-piperidin-1-yl-ethoxy)-phenyl]-5,6,7,8 -tetrahydro-naphthalen-2-ol,
(−)-Cis-6-phenyl-5-[4-(2-pyrrolidin-1-yl-ethoxy)-phenyl]-5,6,7,8-tetrahydro-naphthalen-2-ol,
Cis-6-phenyl-5-[4-(2-pyrrolidin-1-yl-ethoxy)-phenyl]-5,6,7,8-tetrahydro-naphthalen-2-ol,
Cis 1-[6'-pyrrolodinoethoxy-3'-pyridyl]-2-phenyl-6-hydroxy-1,2,3,4-tetrahydrohaphthalene, and
Cis-6-(4'hydroxyphenyl)-5-[4-(2-piperidin-1-yl-ethoxy)-phenyl]-5,6,7,8-tetrahydro-naphthalen-2-ol.

\* \* \* \* \*